(12) United States Patent
Haag et al.

(10) Patent No.: US 12,365,642 B2
(45) Date of Patent: Jul. 22, 2025

(54) METHOD AND APPARATUS FOR PRODUCING GREEN OLEFINS AND GREEN GASOLINE FROM RENEWABLE SOURCES

(71) Applicant: L'Air Liquide, Société Anonyme pour l'Etude et l'Exploitation des Procédés Georges Claude, Paris (FR)

(72) Inventors: Stéphane Haag, Frankfurt am Main (DE); Frank Castillo-Welter, Friedrichsdorf (DE); Bryce Williams, Frankfurt am Main (DE); Nga Thi Quynh Do, Braunschweig (DE); Lin Lin, Frankfurt am Main (DE)

(73) Assignee: L'Air Liquide, Societe Anonyme Pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

(21) Appl. No.: 17/957,283

(22) Filed: Sep. 30, 2022

(65) Prior Publication Data

US 2023/0103301 A1 Apr. 6, 2023

(30) Foreign Application Priority Data

Oct. 1, 2021 (EP) .................................... 21020493

(51) Int. Cl.
*C07C 1/24* (2006.01)
*B01D 3/14* (2006.01)
(Continued)

(52) U.S. Cl.
CPC .......... *C07C 29/1516* (2013.01); *B01D 3/143* (2013.01); *C07C 1/24* (2013.01);
(Continued)

(58) Field of Classification Search
None
See application file for complete search history.

(56) References Cited

U.S. PATENT DOCUMENTS 4,382,843 A * 5/1983 Black ...................... C07C 29/80
 203/45
5,266,188 A * 11/1993 Kukes ..................... C10G 45/08
 208/213
(Continued)

FOREIGN PATENT DOCUMENTS

CN 101591567 A * 12/2009
CN 105713659 A * 6/2016
(Continued)

OTHER PUBLICATIONS

Machine translation CN 101591567. Obtained Sep. 7, 2023 (Year: 2023).*

(Continued)

*Primary Examiner* — In Suk C Bullock
*Assistant Examiner* — Alyssa L Cepluch
(74) *Attorney, Agent, or Firm* — Elwood L. Haynes

(57) ABSTRACT

A method for producing green olefins and green gasoline from renewable sources, the method including: providing $CO_2$ and hydrogen as feed to produce methanol in a methanol reactor, to produce an MTO reaction effluent, reacting the MTO reaction effluent in a plurality of separation columns to separate hydrocarbons, wherein the plurality of separation columns includes a Deethanizer column, a Depropanizer column, and a Debutanizer column, hydrogenating a fraction of separated hydrocarbons in the Debutanizer column with the hydrogen in a hydrogenation reactor, wherein the fraction of separated hydrocarbons from the Debutanizer column includes $C_{5+}$ hydrocarbons; producing the green gasoline and Liquefied Petroleum Gas (LPG) by stabilizing the hydrogenated hydrocarbons in a gasoline stabilizer column; and producing the olefins by separating ethylene from $C_2$ hydrocarbons using a $C_2$ splitter column
(Continued)

and by separating propylene from $C_3$ hydrocarbons using a $C_3$ splitter column.

14 Claims, 10 Drawing Sheets

(51) Int. Cl.
    *C07C 7/00*     (2006.01)
    *C07C 7/04*     (2006.01)
    *C07C 29/151*     (2006.01)
    *C10G 3/00*     (2006.01)
    *C10G 45/32*     (2006.01)

(52) U.S. Cl.
    CPC ............... *C07C 7/005* (2013.01); *C07C 7/04* (2013.01); *C10G 3/42* (2013.01); *C10G 45/32* (2013.01); *C10G 2300/1011* (2013.01); *C10G 2300/305* (2013.01); *C10G 2400/02* (2013.01); *C10G 2400/20* (2013.01)

(56) References Cited

U.S. PATENT DOCUMENTS

| | | | |
|---|---|---|---|
| 5,631,302 A | 5/1997 | König et al. | |
| 5,714,662 A * | 2/1998 | Vora | C07C 41/06 585/638 |
| 6,121,504 A * | 9/2000 | Kuechler | C10G 3/49 585/910 |
| 2004/0020360 A1 * | 2/2004 | Reyes | C07C 7/13 95/143 |
| 2009/0289227 A1 * | 11/2009 | Rising | C25B 1/00 422/600 |
| 2010/0063337 A1 | 3/2010 | Bach et al. | |
| 2012/0083634 A1 * | 4/2012 | Corradi | C10G 11/00 585/324 |
| 2012/0101312 A1 | 4/2012 | Ahlers et al. | |
| 2013/0303819 A1 * | 11/2013 | Su | C07C 1/20 585/639 |
| 2020/0346995 A1 * | 11/2020 | Gaur | C07C 7/163 |
| 2021/0363007 A1 * | 11/2021 | Vicari | C07C 29/80 |
| 2022/0119328 A1 * | 4/2022 | Schroer | C01C 1/02 |

FOREIGN PATENT DOCUMENTS

| | | |
|---|---|---|
| DE | 10 2009 031636 | 1/2011 |
| EP | 0 682 002 | 11/1995 |
| WO | WO 2007 140844 | 12/2007 |
| WO | WO 2012 02134 | 2/2012 |
| WO | WO 2013 076294 | 5/2013 |

OTHER PUBLICATIONS

Machine translation CN 105713659. Obtained Sep. 7, 2023 (Year: 2023).*

European Search Report for corresponding EP 21020493, Mar. 9, 2022.

* cited by examiner

METHOD AND APPARATUS FOR PRODUCING GREEN OLEFINS AND GREEN GASOLINE FROM RENEWABLE SOURCES

CROSS REFERENCE TO RELATED APPLICATIONS

This application claims the benefit of priority under 35 U.S.C § 119 (a) and (b) to European Patent Application No. 21020493.9, filed Oct. 1, 2021, the entire contents of which are incorporated herein by reference.

TECHNICAL FIELD

The present disclosure relates generally to producing hydrocarbons; more specifically, the present disclosure relates to a method and apparatus for producing olefins and gasoline using $CO_2$ and hydrogen from renewable sources, thus, these products are also termed green olefins/gasoline.

BACKGROUND

Concepts for methanol synthesis based on $CO_2$ and hydrogen exist but are not fully optimized for today's challenges such as smaller capacities, integration into other processes, and fluctuating operation conditions. European patent EP 0 682 002 B1 (1995) describes a methanol synthesis setup for $CO_2$ and $H_2$ using a once-through adiabatic pre-reactor. This scheme was optimized for the catalysts available at that time and is shown as a simplified flowsheet. This process set-up aims to boost the CO-content via the reverse water-gas shift reaction (RWGS) in the pre-reactor and therefore have better performance in the subsequent reactor. Based on the better performance of modern catalysts, the single-stage synthesis loop can deliver comparable production capacity, even without the RWGS stage. Thus, a simpler operation is possible at reduced capital investment. Nevertheless, both concepts are close and not optimized to be integrated into a whole process chain to produce green molecules. For the purposes of this disclosure, green molecules are to be understood as molecules or chemicals produced using renewable sources or feedstocks.

The methanol to propylene (MTP) process is a specific form of the oxygenate to olefin (OTO) reaction, or, more specifically, using only methanol as oxygenate, the methanol to olefin (MTO) reaction, aiming at maximizing the propylene yield. The MTP process uses methanol as a feedstock to produce valuable hydrocarbons such as propylene, ethylene, and gasoline. The state-of-the-art MTP plant design, elements of which are described in published international patent application WO 2007/140 844 A1 comprises six process sections, which are Reaction Section, Reactor Regeneration Gas Separation, Hydrocarbon Compressing, Purification (Propylene/LPG/Gasoline), and an optional Ethylene Recovery System and Ethylene Refrigerant System. The methanol feed for the Methanol to Propylene plant can be either as Liquid methanol of storable and transportable quality (e.g. US Federal Specification O-M-232L Grade AA) to be used as reactor feed methanol as well as liquid solvent methanol in the purification or vaporous reactor feed methanol supplied as vapor from an upstream methanol production facility. The liquid solvent methanol is provided in an additional purification step of the upstream methanol production facility. Both methanol grades and their integration with the first reaction step are done as described in DE 10 2009 031 636. Alternatively, liquid solvent methanol may be produced inside the MTP plant. The Reaction Section of the existing MTP plant design includes supplying Reactor feed methanol as well as recycle methanol as vapor overhead stream or as liquid methanol stream of the corresponding separation step. If the reactor feed methanol and/or the recycled methanol is supplied as a liquid, it must be vaporized. The vaporized methanol or the vapor methanol are then superheated to the required feed temperature of the DME Reactor, which is between 250° C. and 280° C. The superheated methanol is fed to the DME Reactor. The DME Reactor can be a one-stage adiabatic fixed-bed reactor where the methanol vapor is partly converted to dimethyl ether (DME) on an aluminum oxide catalyst. The DME and unconverted methanol are fed to the MTP Reactor where oxygenates react to propylene and byproducts including butenes and butanes. Olefins other than propylene are recycled to the MTP Reactor to enhance propylene yield. The overall reaction in the MTP Reactor is exothermic, requiring intermediate cooling to keep the temperature within the desired range. The products of the DME Reactor are fed individually to the different stages of the MTP Reactor. The DME Reactor effluent can be sent to all or some of the stages as two-phase or single phase. The temperature profile in the MTP Reactor can be controlled individually for each reactor stage by adjusting the DME feed temperature and in the case of two-phase flow by adjusting the vapor-liquid ratio of the DME feed to the different stages. The feed to the first stage of the MTP Reactor is mixed with the hydrocarbon recycle stream and with process steam. This mixture is superheated and fed to the MTP Reactor. During the operation of the MTP Reactor, small amounts of heavy hydrocarbons are formed which partly block the active sites of the catalyst. To minimize the carbonization, process steam is added to the feed of the first MTP reaction stage. The steam also serves as a heat sink for the exothermic reaction and thus supports the control of the temperature rise over the catalyst beds. In the subsequent stages, additional reaction water is generated. Therefore, no additional process steam has to be added to the DME/methanol feed to reactor stages. The hydrocarbon recycled to the first MTP reaction stage increases the propylene yield by conversion of olefins other than propylene. In addition, the hydrocarbons serve as a heat sink for the exothermic reaction supporting again the temperature control over the catalyst beds. The product stream leaving the MTP Reactor mainly consists of olefins and process water as well as reaction water. In addition, the reactor effluent contains naphthenes, paraffins, aromatic components, and light ends, i. e. hydrocarbons which are gaseous under ambient conditions and comprise one to four carbon atoms per molecule. These components are formed as by-products of the DME/methanol conversion. Inlet pressure of the MTP reactor shall be as low as possible to favor propylene selectivity. However, plant complexity increases substantially, if the pressure goes below ambient. In addition, pressure drop over the reactor and downstream equipment must be considered. Therefore, good propylene yield can be observed at inlet pressures between 0.1 and 2 bar. A favorable catalyst for the MTP reaction is ZSM-5 zeolite. However, other zeolites or different catalysts systems could be used in principle as well.

The catalyst of each MTP reactor has to be regenerated when DME/Methanol conversion in the respective reactor drops below desired limits. Oxidative regeneration is done and in-situ by controlled combustion of coke deposited on the active surface, including the catalyst pores, of the catalyst with a nitrogen/air mixture. For regeneration one reactor is taken off-line, purged with steam, dried with nitrogen, and then regenerated with a mixture of hot nitrogen and air. The concept of two Reactors in operation and one Reactor in stand-by normally employed in MTP plants allows for regeneration of one Reactor without impact on plant production. The number of reactors is not limited to three.

The Gasoline Purification of the existing MTP plant design includes routing the $C_{4+}$ bottom product of the Debutanizer Column to a Dehexanizer. In this column, $C_{6+}$ hydrocarbons for recycling to the MTP Reaction are separated from $C_{7+}$ hydrocarbons. The top product from the Dehexanizer is split into two streams. A larger part is vaporized and sent as $C_5/C_6$ recycle to the hydrocarbon recycle. The smaller part, the $C_5/C_6$ purge is relieved from residual $C_4$ in the Gasoline Stabilizer Column. The operation of this column allows adjusting the vapor pressure of the gasoline product. The bottoms product of both the Dehexanizer and the Gasoline Stabilizer form the MTP Gasoline product. To prevent polymerization an oxidation inhibitor may be added to the condensers and reboilers of any or all of the Debutanizer, Dehexanizer, and Gasoline Stabilizer Column. As hydrocarbon recycling plays an important role in the propylene yield of the MTP plant, both overall flow rate and composition have to be carefully controlled. The split of the different streams can be adjusted over a catalyst lifetime to maximize those streams most beneficial to propylene yield. The composition of the resulting gasoline product is rich in Olefins and by SOR (Selective Olefin Recovery) contains also significant amounts of aromatics.

Downscaling to small-scale units and the utilization of unconventional feedstock like pure $CO_2$ to produce methanol makes the whole process more challenging and less economical. The catalyst of each MTP reactor has to be regenerated when DME/Methanol conversion in the respective reactor drops below desired limits. Regeneration is done in-situ by controlled combustion of coke with a nitrogen/air mixture. For regeneration, one reactor is taken off-line, purged with steam, dried with nitrogen, and then regenerated with a mixture of hot nitrogen and air. Further, a costly ASU (Air Separation Unit) is then required for only periodic utilization. The gasoline produced in the State-of-the-Art process is not pump grade as higher amounts of olefins and aromatics are present. The utilization of a high amount of water is detrimental for MTP catalyst lifetime but useful to ensure high propylene selectivity through dedicated diluting partial pressure of reactants in the reaction system.

Therefore, there is a need to address the aforementioned technical drawbacks in existing technologies for producing green olefins and green gasoline using $CO_2$ and hydrogen from renewable sources.

SUMMARY

The present disclosure seeks to provide a more efficient method and apparatus for producing green light olefins and green pump grade gasoline using $CO_2$ and hydrogen from renewable sources. The present disclosure aims to provide a solution that overcomes, at least partially, the problems encountered in prior art and provide an improved method and apparatus for producing green light olefins and green pump grade gasoline with a 4 steps process including water electrolysis and $CO_2$ feedstock, once-through methanol conversion (or optionally with recycle), once-through methanol to olefins reaction (optionally with recycle) and a separation section including valorization of heavy hydrocarbons through a hydrogenation step. The utilization of the feedstock such as $H_2$, $CO_2$ in a circular approach allows better performances in different areas of reaction path and huge flexibility of size and location combined with high-quality products. The object of the present disclosure is achieved according to a general aspect of the invention by the solutions provided in the enclosed independent claims. Advantageous implementations of the present disclosure according to specific aspects of the invention are further defined in the dependent claims.

According to a first aspect, the present disclosure provides a method for producing olefins and gasoline from renewable sources, the method comprising:

providing $CO_2$ and hydrogen as feed to produce methanol in a methanol reactor, wherein the hydrogen is obtained from a water electrolyzer;

reacting the methanol in an isothermal Methanol-to-Olefin (MTO) reactor to produce an MTO reaction effluent comprising olefinic and non-olefinic hydrocarbons and water, wherein the water produced during a MTO reaction in the isothermal MTO reactor is used at least partially as feed for the water electrolyzer, wherein non-converted $CO_2$ from the methanol reactor is directed at least partially into the isothermal MTO reactor;

treating the MTO reaction effluent in a plurality of separation columns to separate hydrocarbons, wherein the plurality of separation columns comprises a Deethanizer column, a Depropanizer column, a Debutanizer column, a $C_2$ splitter column, and a $C_3$ splitter column, wherein the separation of the hydrocarbons from the MTO reaction effluent comprises (i) separating $C_2$ hydrocarbons from $C_{3+}$ hydrocarbons at the Deethanizer column (106), (ii) separating ethylene from the $C_2$ hydrocarbons at the $C_2$ splitter column, (iii) separating $C_3$ hydrocarbons from $C_{4+}$ hydrocarbons at the Depropanizer column (108), (iv) separating propylene from the $C_3$ hydrocarbons at the $C_3$ splitter column, and (v) separating $C_4$ hydrocarbons as a Debutanizer overhead fraction at the Debutanizer column (110), wherein a fraction of the separated hydrocarbons settles at a bottom of the Debutanizer column (110) as a Debutanizer bottom fraction after separation, wherein the Debutanizer bottom fraction comprises $C_{5+}$ hydrocarbons;

hydrogenating at least a part of the Debutanizer bottom fraction with the hydrogen obtained from the water electrolyzer in a hydrogenation reactor to obtain a hydrogenated Debutanizer bottom fraction;

routing out at least a part of the hydrogenated Debutanizer bottom fraction as gasoline product, or separating Liquefied Petroleum Gas (LPG) from the hydrogenated Debutanizer bottom fraction in a gasoline stabilizer column (114), routing out a LPG product as a gasoline stabilizer column overhead fraction, and routing out a stabilized gasoline product as a gasoline stabilizer column bottom fraction; and routing out an olefin product, comprising propylene and optionally at least a part of the ethylene.

The method for producing the green olefins and the green gasoline from the renewable sources according to the present disclosure is of advantage in that the method enables the production of the green olefins and the green gasoline from clean/green educts that include $H_2$ from electrolysis, and $CO_2$ based MeOH synthesis. The method enables the production of the green olefins and the green gasoline from the renewable sources by utilizing feedstock such as $H_2$, $CO_2$ in a circular approach that enables better performances in different areas of reaction path and huge flexibility of size and location combined with high-quality products.

According to a second aspect, the present disclosure provides an apparatus for producing green olefins and green gasoline from renewable sources, the apparatus comprising:
- a water electrolyzer;
- a methanol reactor, for producing methanol from $CO_2$ and hydrogen, wherein the hydrogen is obtained from a water electrolyzer;
- a Methanol-to-Olefin (MTO) reactor, preferably being designed to be operated isothermally, for reacting the methanol to produce an MTO reaction effluent, wherein water produced during a MTO reaction in the isothermal Methanol-to-Olefin (MTO) reactor is used as feed for the water electrolyzer, wherein non-converted $CO_2$ from the methanol reactor is directed at least partially into the isothermal MTO reactor;
- a plurality of separation columns for treating the MTO reaction effluent to separate hydrocarbons, wherein the plurality of separation columns comprises a Deethanizer column (106), a Depropanizer column (108), a Debutanizer column (110), a $C_2$ splitter column (116), and a $C_3$ splitter column (117), wherein the plurality of separation columns is configured to:
  (i) separate $C_2$ hydrocarbons from $C_{3+}$ hydrocarbons at the Deethanizer column (106),
  (ii) separate ethylene from the $C_2$ hydrocarbons at the $C_2$ sputter column,
  (iii) separate $C_3$ hydrocarbons from $C_{4+}$ hydrocarbons at the Depropanizer column (108),
  (iv) separate propylene from the $C_3$ hydrocarbons at the $C_3$ splitter column, and
  (v) separate $C_4$ hydrocarbons as a Debutanizer overhead fraction at the Debutanizer column (110), wherein a fraction of the separated hydrocarbons settles at a bottom of the Debutanizer column (110) as a Debutanizer bottom fraction after separation, wherein the Debutanizer bottom fraction comprises $C_{5+}$ hydrocarbons;
- a hydrogenation reactor for hydrogenating at least a part of the Debutanizer bottom fraction with the hydrogen obtained from the water electrolyzer to obtain a hydrogenated Debutanizer bottom fraction;
- optionally a gasoline stabilizer column for stabilizing the hydrogenated Debutanizer bottom fraction to produce a gasoline product and a Liquefied Petroleum Gas (LPG) product.

The apparatus for producing the green light olefins and the green pump grade gasoline using $CO_2$ and hydrogen from the renewable sources according to present disclosure enables the production of green light olefins and green pump grade gasoline from clean/green educts that include $H_2$ from electrolysis, and $CO_2$ based MeOH synthesis. The apparatus enables utilizing feedstock such as $H_2$, $CO_2$ in a circular approach that allows better performances in different areas of reaction path and huge flexibility of size and location combined with high-quality products.

Embodiments of the present disclosure eliminate the aforementioned drawbacks in existing known approaches for producing green olefins and green gasoline from renewable sources. The advantage of the embodiments according to the present disclosure is that the embodiments enable the production of green olefins and green gasoline from renewable sources by utilizing feedstock such as $H_2$, $CO_2$ in a circular approach that allows better performances in the different areas of the reaction path and huge flexibility of size and location combined with high-quality products. The apparatus for green olefins and green gasoline production from the renewable sources can be fully optimized for smaller capacities for local production and integration into other processes and fluctuating operation conditions.

Additional aspects, advantages, features, and objects of the present disclosure are made apparent from the drawings and the detailed description of the illustrative embodiments construed in conjunction with the appended claims that follow. It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. To illustrate the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, the same elements have been indicated by identical numbers. Embodiments of the present disclosure will now be described, by way of example only, with reference to the following diagrams wherein.

DETAILED DESCRIPTION OF EMBODIMENTS

Figure 1:
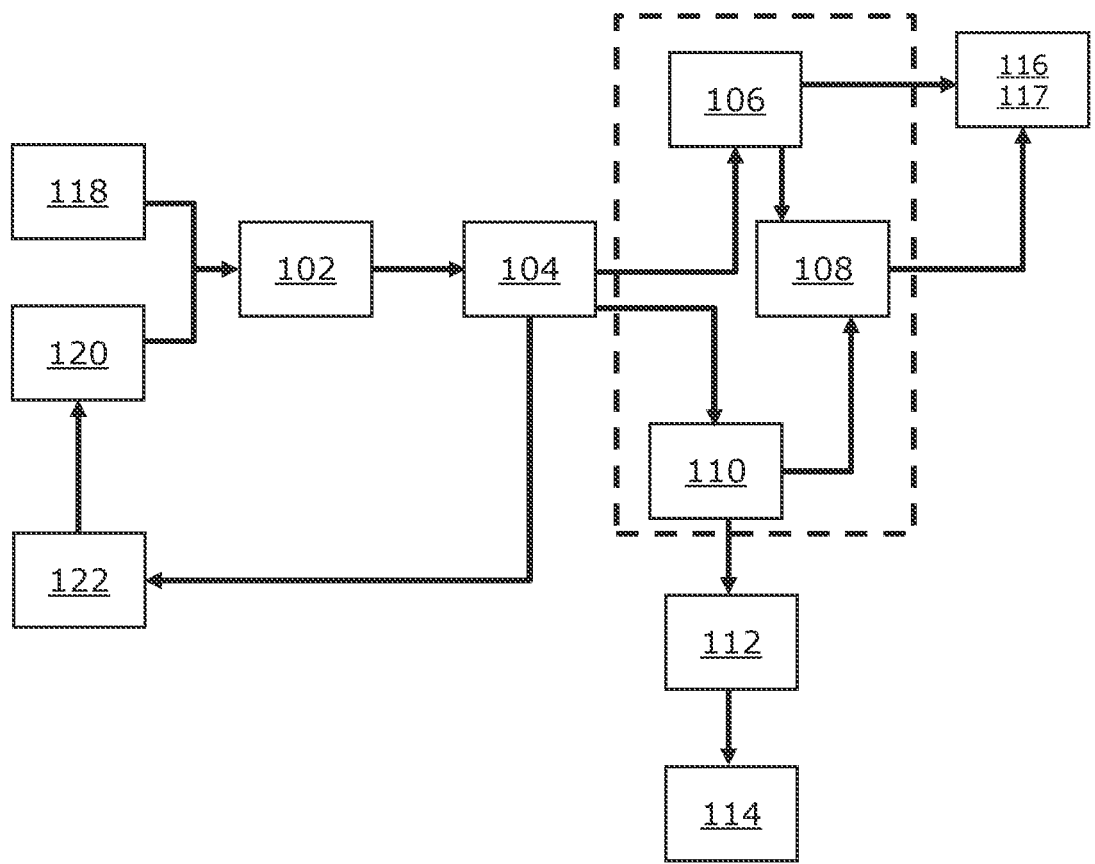
FIG. 1 is a schematic illustration of an apparatus for producing olefins and gasoline from renewable sources according to an embodiment of the present disclosure.

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

According to a first aspect, the present disclosure provides a method for producing olefins and gasoline from renewable sources, the method comprising:

providing $CO_2$ and hydrogen as feed to produce methanol in a methanol reactor, wherein the hydrogen is obtained from a water electrolyzer;

reacting the methanol in a Methanol-to-Olefin (MTO) reactor, preferably an isothermal MTO reactor, to produce a MTO reaction effluent comprising olefinic and non-olefinic hydrocarbons and water, wherein the water in the MTO reaction effluent is used at least partially as feed for the water electrolyzer, wherein non-converted $CO_2$ from the methanol reactor is directed at least partially into the MTO reactor;

treating the MTO reaction effluent in a plurality of separation columns to separate the hydrocarbons, wherein the plurality of separation columns comprises a Deethanizer column, a Depropanizer column, a Debutanizer column, a $C_2$ splitter column, and a $C_3$ splitter column, wherein the separation of the hydrocarbons from the MTO reaction effluent comprises (i) separating $C_2$ hydrocarbons from $C_{3+}$ hydrocarbons at the Deethanizer column, (ii) separating ethylene from the $C_2$ hydrocarbons at the $C_2$ splitter column, (iii) separating $C_3$ hydrocarbons from $C_{4+}$ hydrocarbons at the Depropanizer column, (iv) separating propylene from the $C_3$ hydrocarbons at the $C_3$ splitter column, and (v) separating $C_4$ hydrocarbons as a Debutanizer overhead fraction at the Debutanizer column, wherein a fraction of the separated hydrocarbons settles at a bottom of the Debutanizer column as a Debutanizer bottom fraction after separation, wherein the Debutanizer bottom fraction comprises $C_{5+}$ hydrocarbons;

hydrogenating at least a part of the Debutanizer bottom fraction with the hydrogen obtained from the water electrolyzer in a hydrogenation reactor to obtain a hydrogenated Debutanizer bottom fraction;

routing out at least a part of the hydrogenated Debutanizer bottom fraction as gasoline product, or separating Liquefied Petroleum Gas (LPG) from the hydrogenated Debutanizer bottom fraction in a gasoline stabilizer column, routing out a LPG product as a gasoline stabilizer column overhead fraction, and routing out a stabilized gasoline product as a gasoline stabilizer column bottom fraction; and routing out an olefin product, comprising propylene and optionally at least a part of the ethylene.

The method for producing the green olefins and the green gasoline from the renewable sources according to the present disclosure is of advantage in that the method enables the production of green olefins and green gasoline from clean/green educts that include $H_2$ from electrolysis, and $CO_2$ based MeOH synthesis. The method enables the production of the green olefins and the green gasoline from the renewable sources by utilizing feedstock such as $H_2$, $CO_2$ in a circular approach that enables better performances in different areas of the reaction path and huge flexibility of size and location combined with high-quality products. The method provides a smart way to convert and utilize $CO_2$ to produce the green olefins as well as the green pump grade and sulfur-free gasoline.

A clean $CO_2$ source is combined with hydrogen which is obtained by electrolyzing water in the water electrolyzer is directed into the methanol reactor for producing methanol. The clean $CO_2$ source may enable the production of methanol and water in the methanol reactor in such proportion that no separation is required. The methanol produced in the methanol reactor is reacted in the isothermal Methanol-to-Olefin (MTO) reactor to produce an MTO reaction effluent. The water produced during the MTO reaction in the isothermal MTO reactor is used as feed for the water electrolyzer. The non-converted $CO_2$ from the methanol reactor is directed into the isothermal MTO reactor that enables to lower partial pressure in the MTO reactor. The non-converted $CO_2$ and the additional $CO_2$ going into the MTO reactor increase propylene selectivity by lowering the partial pressure of reactants such as methanol and olefins. The amount of water entering the MTO reactor may be lowered to extend catalyst lifetime without losing propylene selectivity. The MTO reactor may preferably be designed to be operated isothermally, e. g. radial with plates or horizontal with plates. Optionally, the MTO reactor includes a salt bath and tubes for small applications.

The MTO reaction effluent is reacted in the plurality of separation columns to separate hydrocarbons, as defined in the independent claims of this disclosure.

Optionally, the separation of hydrocarbons in the plurality of separation columns includes (i) treating the MTO reaction effluent in the Deethanizer column, wherein the Deethanizer column produces a Deethanizer overhead vapor fraction that is rich in ethane and ethylene, and a Deethanizer bottom fraction that is rich in $C_{3+}$ hydrocarbons, and (ii) treating the Deethanizer bottom fraction that is rich in $C_{3+}$ hydrocarbons in the Depropanizer column to produce a Depropanizer overhead vapor fraction that is rich in propane and propylene, and a Depropanizer bottom fraction that is rich in $C_{4+}$ hydrocarbons, wherein the Depropanizer bottom fraction rich in $C_{4+}$ hydrocarbons comprises 20-50% of $C_4$ olefins and 50 to 80% of $C_4$ paraffins, wherein the Depropanizer bottom fraction is at least partially directed to the hydrogenation reactor for hydrogenation.

A higher contribution comes from iso-butylene with 30 to 60% of all the $C_4$ olefins in the stream and mostly iso-butane with over 60% of all the $C_4$ paraffins in the stream.

Optionally, when the plurality of separation columns comprises a dehexanizer column, the separation of hydrocarbons in the plurality of separation columns comprises (i) treating the Debutanizer bottom fraction that is rich in $C_{5+}$ hydrocarbons in the Dehexanizer column to produce a Dehexanizer overhead vapor fraction that is rich in hexane and hexene, and a Dehexanizer bottom fraction that is rich in $C_{7+}$ hydrocarbons, wherein the Dehexanizer bottom fraction is directed to the hydrogenation reactor for hydrogenation.

The hydrogenation of Dehexanizer bottom fraction delivers a colorless product within specification margin on olefins and aromatics content.

Optionally, the $C_2$ splitter column separates ethylene from ethane, the $C_3$ splitter column separates propylene from propane, the ethylene and propylene are comprised in the overhead fractions of the $C_2$ splitter column and the $C_3$ splitter column, and the propane is directed at least partially to the hydrogenation reactor.

The $C_2$ splitter and the $C_3$ splitter are operated at high pressure, utilizing closed-cycle propylene, and ethylene refrigeration.

Optionally, at least a part of the ethylene is converted into ethanol and added to the gasoline product or stabilized gasoline product to increase the Research Octane Number (RON) and/or the Motor Octane Number (MON) of the gasoline.

The addition of the ethanol enables to stabilize the gasoline and the increase of the RON and MON of the gasoline improves ignition and combustion efficiency, thereby reducing pollution emissions.

Optionally, the method includes scrubbing the $CO_2$ from the MTO reaction effluent using a $CO_2$ scrubber to avoid the formation of solid $CO_2$. At least a part of the scrubbed $CO_2$ is provided as feed into the methanol reactor and the isothermal MTO reactor. Optionally, the $CO_2$ scrubber is a chemical scrubber. The chemical $CO_2$ scrubber uses caustic (NaOH solution) that can wash out bulk $CO_2$ from the quenched MTO reaction effluent for recycling. Optionally, the $CO_2$ scrubber is a physical scrubber. In an example, the physical scrubber is operated with methanol as washing agent, preferably methanol produced in the methanol reactor and optionally purified.

Optionally, the $CO_2$ scrubber is arranged upstream of the plurality of separation columns. Optionally, the $CO_2$ scrubber includes a $CO_2$ adsorbent or a guard bed to remove final traces of $CO_2$ before reacting the quenched MTO reaction effluent in the plurality of separation columns to separate hydrocarbons, as $CO_2$ can form dry ice at cryogenic temperatures in the plurality of separation columns e.g., Demethanizer or Deethanizer and may block the equipment from functioning. The scrubbed $CO_2$ is more preferably directed into the isothermal MTO reactor as the $CO_2$ stream is probably not so pure.

Optionally, the $CO_2$ scrubber is arranged downstream of the Deethanizer, as shown in the figures. However, arranging the $CO_2$ scrubber upstream of the plurality of separation columns is generally preferred due to the reasons discussed above, and the skilled practitioner will interpret the figures so as to shift the $CO_2$ scrubber to such upstream position.

Optionally, when the plurality of separation columns comprises a Demethanizer column, the method comprises directing the Deethanizer overhead vapor fraction into the Demethanizer column to produce an overhead fraction comprising methane.

Optionally, the method comprises directing at least a part of the overhead fraction from the Demethanizer column into the methanol reactor. The overhead fraction from the Demethanizer comprises methane, but also carbon monoxide, carbon dioxide, and hydrogen. Routing the overhead fraction from the Demethanizer column back into the methanol reactor increases the methanol yield. The methane comprised in the Demethanizer overhead fraction is an inret component in the methanol reactor and in the MTO reactor, and thus helps to reduce the methanol partial pressure in the MTO reactor which is increases the ethylene and propylene yield and also the catalyst lifetime.

Optionally, the method comprises recycling at least one element, selected from the following group:

(i) the Depropanizer bottom fraction that is rich in $C_{4+}$ hydrocarbons, (ii) the Debutanizer bottom fraction that is rich in $C_{5+}$ hydrocarbons, (iii) the ethylene from the $C_2$ splitter column overhead fraction, (iv) the propane from the $C_3$ splitter column overhead fraction, at least partially into the MTO reactor. All of these elements can increase the ethylene and propylene yield, either by being converted to these light olefins, or by reducing the methanol partial pressure in the MTO reactor, or by a mixture of both effects.

Optionally, the method comprises quenching the MTO reaction effluent by treating the MTO reaction effluent with water before separating the MTO reaction effluent in the plurality of separation columns, wherein the water after quenching is directed at least partially into the water electrolyzer (122), optionally after water purification. The amount of fresh water supply is thus reduced.

Optionally, the $CO_2$ used as the feed to produce methanol is free of sulfur components and amines therein. Both component groups may act as catalyst poisons either in the methanol reactor, or in the MTO reactor, or in both.

Optionally, the methanol produced in the methanol reactor is purified in a distillation column which is operated under a pressure ranging between 25 bar to 125 bar, and a temperature ranging between 200° C. and 350° C. The methanol may be produced using a single-stage reaction by directly reacting $CO_2$ and $H_2$. The methanol may be produced using a multi-stage reaction, where the $CO_2$ first converted into CO through reverse water gas shift (RWGS). Inter-stage condensation and separation may be performed because an increase in carbon conversions may be achieved when methanol and water are condensed. Not all $CO_2$ has to be converted for methanol production but most of the Hydrogen has to be converted in a once-through methanol reactor concept for producing green olefins and green gasoline without recycling. A part of the $CO_2$ may be used as a diluting agent to replace the water in the isothermal Methanol-to-Olefin (MTO) reactor. The purge gas with $CO_2$ and $H_2$ may also be directed into the MTO the isothermal Methanol-to-Olefin (MTO) reactor. Optionally, the $H_2$ is separated from $CO_2$ before directing into the isothermal Methanol-to-Olefin (MTO) reactor.

Optionally, the methanol produced in the methanol reactor is a methanol-water mixture comprising in a range of 62 to 66 weight by percentage (wt-%) of methanol and about 34 to 38 weight by percentage (wt-%) of water. In an example, this methanol-water mixture may be fed into the MTO reactor without further separation, purification, or other treatment.

Optionally, the methanol-water mixture is reacted directly without any treatment in the MTO reactor. Hence, the requirement of DME Reactor where methanol vapor is partly converted to dimethyl ether (DME) is avoided.

Optionally, the methanol from the methanol reactor is separated from the water depending on an amount of $CO_2$ available for the reaction to remove oxygenate in the MTO reactor. Optionally, the separated methanol is used as a fuel for Gas turbines. The percentage of separation of water depends on the amount of $CO_2$ available for the reaction. Optionally, the $CO_2$ used as a diluting agent. The amount of water used may be reduced accordingly to the amount of $CO_2$ that may be sent to the isothermal MTO reactor. For example, if 20-30% of the $CO_2$ is not converted, then 20-30% of the water may be removed. The removal of water corresponding to the amount of $CO_2$ extends the lifetime of the catalyst in the isothermal MTO reactor and facilitates methanol synthesis at lower pressure in the methanol reactor as the conversion of all the $CO_2$ is not required.

Optionally, the method comprises directing a purge gas with $CO_2$ and $H_2$ obtained from the methanol reactor into the isothermal MTO reactor. This is an alternative option to reduce the methanol partial pressure in the MTO reactor.

Optionally, the non-converted $CO_2$ that is directed into the isothermal MTO reactor optimizes a partial pressure of reactants in the isothermal MTO reactor and increases a lifetime of a catalyst included in the isothermal MTO reactor. The non-converted $CO_2$ may have a beneficial effect on carbon formation on the catalyst in the Methanol-to-Olefin (MTO) reactor. The non-converted $CO_2$ inhibits the formation of coke in the Methanol-to-Olefin (MTO) reactor. The non-converted $CO_2$ from the methanol synthesis with additional $CO_2$ going into the MTO reactor allows better catalyst lifetime because of using less water than in the state of the art process.

Optionally, the $CO_2$ is used as a diluting agent for the hydrogenation of the separated hydrocarbons. Adding diluting agents helps to limit the exothermicity of the hydrogenation reaction and avoids the formation of hot spots in the hydrogenation catalyst bed. The use of $CO_2$ as diluting agent helps to save other inert gases like nitrogen.

Optionally, the $CO_2$ and the hydrogen are used as diluting agents during oxidative regeneration of the catalyst in the isothermal MTO reactor. Optionally, Oxygen obtained by electrolyzing water in the water electrolyzer is used along with $CO_2$ for regeneration. Hydrogen present in a minimal amount in the oxygen stream may be removed using membranes. The hydrogen molecule can dissociate into atoms on the surface of the membrane that is only permeable to hydrogen and then diffuse through the membrane lattice. Optionally, the membrane is a dense metal membrane that separates hydrogen with infinite selectivity.

Optionally, the method includes performing the MTO reaction in the MTO reactor (104), preferably in an isothermal MTO reactor (104), at a temperature in a range of 400 to 550° C., most preferably 420 to 480° C., and at a pressure in a range of 0.2 to 5 bara, most preferably 1 to 1.5 bara, to increase the $C_3$ hydrocarbons yield in the MTO reaction effluent.

Optionally, the method includes using gasification of at least a part of hydrocarbon fractions, selected from the following group:
Debutanizer bottom fraction,
Depropanizer bottom fraction,
C3 splitter column bottom fraction;
wherein products of the gasification comprising the hydrogen and the $CO_2$ are used as feed for producing the methanol in the methanol reactor.

Optionally, the method includes obtaining $CO_2$ from a biomass gasification utilizing oxygen from the water electrolyzer.

According to a second aspect, the present disclosure provides an apparatus for producing olefins and gasoline from renewable sources, the apparatus comprising:
a water electrolyzer (122);
a methanol reactor for producing methanol from $CO_2$ and hydrogen, wherein the hydrogen is obtained from the water electrolyzer;
a Methanol-to-Olefin (MTO) reactor, preferably being designed to be operated isothermally, for reacting the methanol to produce an MTO reaction effluent, wherein water produced during an MTO reaction in the Methanol-to-Olefin (MTO) reactor is used as feed for the water electrolyzer, wherein non-converted $CO_2$ from the methanol reactor is directed at least partially into the MTO reactor;
a plurality of separation columns for treating the MTO reaction effluent to separate hydrocarbons, wherein the plurality of separation columns comprises a Deethanizer column, a Depropanizer column, a Debutanizer column, a $C_2$ splitter column, and a $C_3$ splitter column, wherein the plurality of separation columns is configured to:
(i) separate $C_2$ hydrocarbons from $C_{3+}$ hydrocarbons at the Deethanizer column,
(ii) separate ethylene from the $C_2$ hydrocarbons at the $C_2$ splitter column,
(iii) separate $C_3$ hydrocarbons from $C_{4+}$ hydrocarbons at the Depropanizer column,
(iv) separate propylene from the $C_3$ hydrocarbons at the $C_3$ splitter column, and
(v) separate $C_4$ hydrocarbons as a Debutanizer overhead fraction at the Debutanizer column, wherein a fraction of the separated hydrocarbons settles at a bottom of the Debutanizer column as a Debutanizer bottom fraction after separation, wherein the Debutanizer bottom fraction comprises $C_{5+}$ hydrocarbons;
a hydrogenation reactor for hydrogenating at least a part of the Debutanizer bottom fraction with the hydrogen obtained from the water electrolyzer to obtain a hydrogenated Debutanizer bottom fraction;
optionally a gasoline stabilizer column for stabilizing the hydrogenated Debutanizer bottom fraction to produce a gasoline product and a Liquefied Petroleum Gas (LPG) product.

The apparatus for producing the green light olefins and the green pump grade gasoline using $CO_2$ and hydrogen from the renewable sources according to present disclosure enables the production of the green light olefins and the green pump grade gasoline from clean/green educts that include $H_2$ from electrolysis, and $CO_2$ based MeOH synthesis. The apparatus enables utilizing feedstock such as $H_2$, $CO_2$ in a circular approach that enables better performances in the different areas of the reaction path and huge flexibility of size and location combined with high-quality products. The apparatus for producing the green olefins and the green gasoline from the renewable sources can be fully optimized for smaller capacities for local production and integration into other processes and fluctuating operation conditions.

Embodiments of the present disclosure substantially eliminate or at least partially address the aforementioned technical drawbacks in existing technologies in providing a system and method for producing green light olefins and green pump grade utilizing $H_2$ and $CO_2$ from renewable resources.

DETAILED DESCRIPTION OF THE DRAWINGS

FIG. 1 is a schematic illustration of an apparatus 100 for producing green olefins and green gasoline from renewable sources according to an embodiment of the present disclosure. The apparatus 100 includes a methanol reactor 102, an isothermal Methanol-to-Olefin (MTO) reactor 104, a plurality of separation columns comprising a Deethanizer column 106, a Depropanizer column 108, and a Debutanizer column 110, a hydrogenation chamber 112, a gasoline stabilizer 114, a $C_2$ splitter column 116, a $C_3$ splitter column 117 (shown together with 116 as one block for simplification, but 117 representing a separate separation column), and a water electrolyzer 122. For the purposes of this disclosure, the separation columns are to be understood as performing the separation by distillation or rectification, unless otherwise specified. The methanol reactor 102 produces methanol from $CO_2$ and hydrogen. The $CO_2$ is obtained from a $CO_2$ feed chamber 118 and the hydrogen is obtained from a hydrogen feed chamber 120. The hydrogen is produced by electrolyzing water in the water electrolyzer 122. The isothermal Methanol-to-Olefin (MTO) reactor 104 reacts the methanol produced in the methanol reactor 102 to produce an MTO reaction effluent. The water produced during MTO reaction in the isothermal Methanol-to-Olefin (MTO) reactor 104 is used as feed for the water electrolyzer 122. Non-converted $CO_2$ from the methanol reactor 102 is directed into the isothermal Methanol-to-Olefin (MTO) reactor 104. The Deethanizer column 106, the Depropanizer column 108, and the Debutanizer column 110 treats the MTO reaction effluent produced in the isothermal Methanol-to-Olefin (MTO) reactor 104 to separate hydrocarbons from the MTO reaction effluent. The Deethanizer column 106 separates $C_2$ hydrocarbons from $C_{3+}$ hydrocarbons. The Depropanizer column 108 separates $C_3$ hydrocarbons from $C_{4+}$ hydrocarbons. The Debutanizer column 110 separates $C_4$ hydrocarbons from $C_{5+}$ hydrocarbons. A fraction of the separated hydrocarbons comprising $C_{5+}$ hydrocarbons settles at a bottom of the Debutanizer column 110 after separation. The hydrogenation reactor 112 hydrogenates the fraction of separated hydrocarbons settled at the bottom of the Debutanizer column 110 with the hydrogen obtained from the water electrolyzer 122. The gasoline stabilizer column 114 stabilizes hydrogenated hydrocarbons from the hydrogenation reactor 112 to produce the green gasoline as bottom fraction and Liquefied Petroleum Gas (LPG) as overhead fraction. The $C_2$ splitter column 116 and $C_3$ splitter column 117 produces ethylene and propylene as the green olefins by splitting the remaining separated hydrocarbons from the plurality of separation columns comprising the Deethanizer column 106, the Depropanizer column 108, and the Debutanizer column 110. Ethylene and propylene are recovered as overhead fractions of the respective splitter columns 116 and 117.

Figure 2:
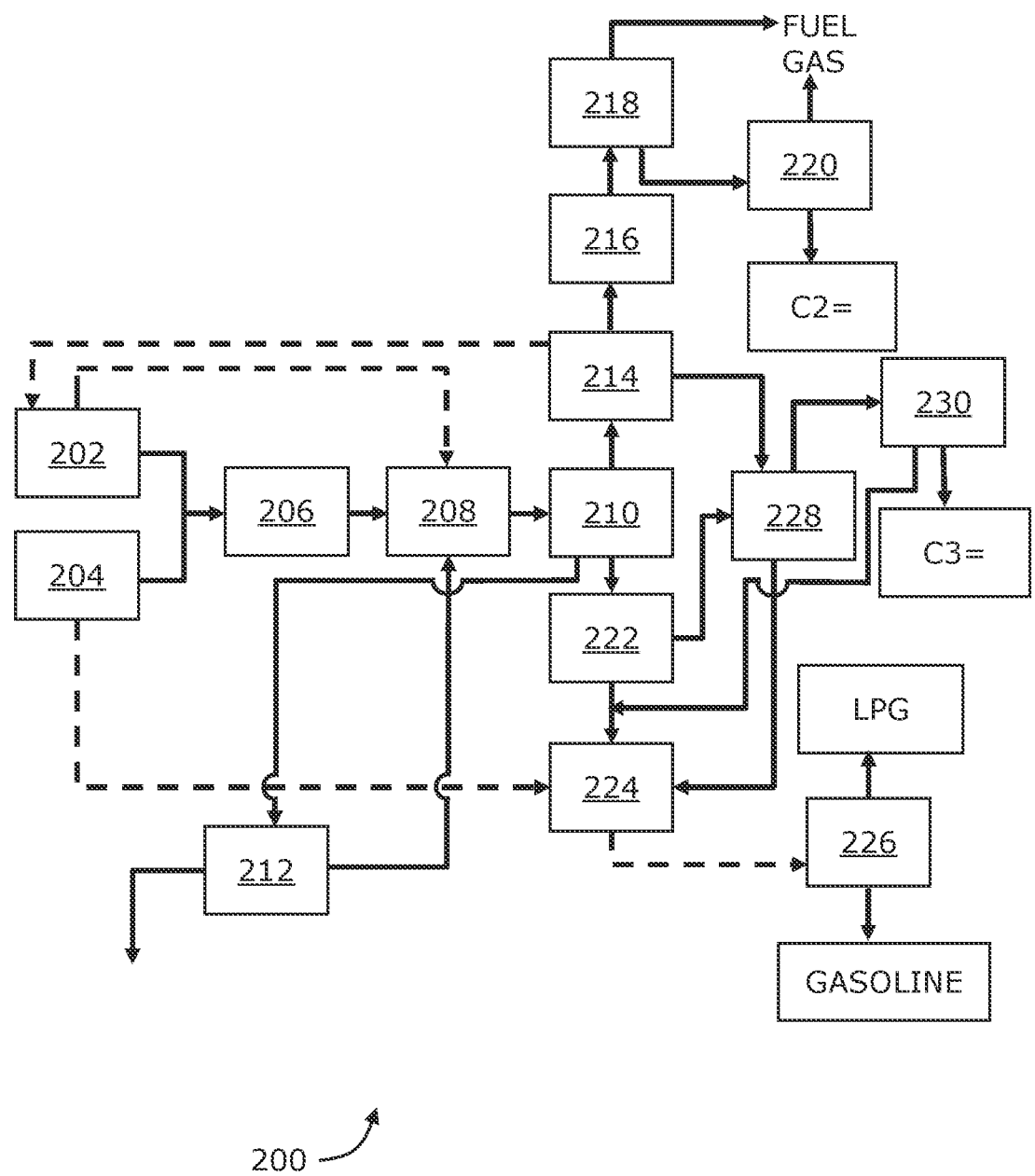
FIG. 2 is a schematic illustration of a once-through process for producing olefins and gasoline from renewable sources utilizing scrubbed $CO_2$ as a feed for producing methanol and Methanol-to-Olefin (MTO) reaction according to an embodiment of the present disclosure.

FIG. 2 is a schematic illustration of a once-through process 200 for producing green olefins and green gasoline from renewable sources utilizing scrubbed $CO_2$ as a feed for producing methanol and Methanol-to-Olefin (MTO) reaction according to an embodiment of the present disclosure. At a step 202, $CO_2$ is obtained from a $CO_2$ feed chamber. At a step 204, hydrogen is obtained from a hydrogen feed chamber. The hydrogen is produced by electrolyzing water in a water electrolyzer 212 and supplied to the hydrogen feed chamber 204 (not shown). At a step 206, methanol is produced in a methanol reactor by utilizing the $CO_2$ obtained from the $CO_2$ feed chamber and the Hydrogen obtained from the hydrogen feed chamber. At a step 208, the methanol is reacted in an isothermal Methanol-to-Olefin (MTO) reactor to produce an MTO reaction effluent. Non-converted $CO_2$ from the methanol reactor is directed into the isothermal Methanol-to-Olefin reactor (MTO) 208. Optionally, a part of the $CO_2$ obtained from the $CO_2$ feed chamber is directed into the isothermal Methanol-to-Olefin (MTO) reactor 208 as diluting agent for the MTO reaction. At a step 210, the MTO reaction effluent is quenched by treating the MTO reaction effluent with water in a quenching chamber. At a step 212, the quenched water is supplied as a feed to the water electrolyzer. At a step 214, the $CO_2$ from the quenched MTO reaction effluent is scrubbed using a $CO_2$ scrubber. The scrubbed $CO_2$ is directed into the $CO_2$ feed chamber. At a step 216, the MTO reaction effluent is reacted in a Deethanizer column for separating $C_2$ hydrocarbons from $C_{3+}$ hydrocarbons. The Deethanizer column produces a Deethanizer overhead vapor fraction that is rich in ethane and ethylene and a Deethanizer bottom fraction that is rich in $C_{3+}$ hydrocarbons. At a step 218, the Deethanizer overhead vapor fraction is reacted in a Demethanizer column for separating $C_1$ hydrocarbons from $C_{2+}$ hydrocarbons. The Demethanizer column produces a Demethanizer overhead vapor fraction rich in $CH_4$, $CO_2$, $H_2$, and CO and a Demethanizer bottom fraction that is rich in $C_{2+}$ hydrocarbons comprising olefins and paraffins. The Demethanizer overhead vapor fraction that is rich in methane is used as fuel gas and/or can be recycled at least partially to the methanol reactor. At a step 220, $C_2$ olefins are separated from $C_2$ paraffins in a $C_2$ splitter column. The $C_2$ paraffins from the $C_2$ splitter are used as fuel gas. At a step 222, the quenched MTO reaction effluent is reacted in a Debutanizer column for separating $C_4$ hydrocarbons from $C_{5+}$ hydrocarbons. A fraction of separated hydrocarbons comprising $C_{5+}$ hydrocarbons settles at a bottom of the Debutanizer column after the reaction. At a step 224, the fraction of separated hydrocarbons in the Debutanizer column is hydrogenated with the hydrogen from the hydrogen feed chamber. The fraction of separated hydrocarbons from the Debutanizer column comprises $C_{5+}$ hydrocarbons. At a step 226, the hydrogenated hydrocarbons are stabilized in a gasoline stabilizer column to produce green gasoline as bottom product and Liquefied Petroleum Gas (LPG) as overhead product. At a step 228, the Deethanizer bottom fraction that is rich in $C_{3+}$ hydrocarbons and a Debutanizer overhead vapor fraction rich in butane and butylene are treated in a Depropanizer column to produce a Depropanizer overhead vapor fraction that is rich in propane and propylene and a Depropanizer bottom fraction that is rich in $C_{4+}$ hydrocarbons. The Depropanizer bottom fraction is directed into a hydrogenation reactor for hydrogenation. At a step 230, the propylene is separated from the propane in the Depropanizer overhead vapor fraction in a $C_3$ splitter. The propane from the $C_3$ splitter is directed along with the fraction of separated hydrocarbons from the Debutanizer column into the hydrogenation reactor for hydrogenation.

Figure 3:
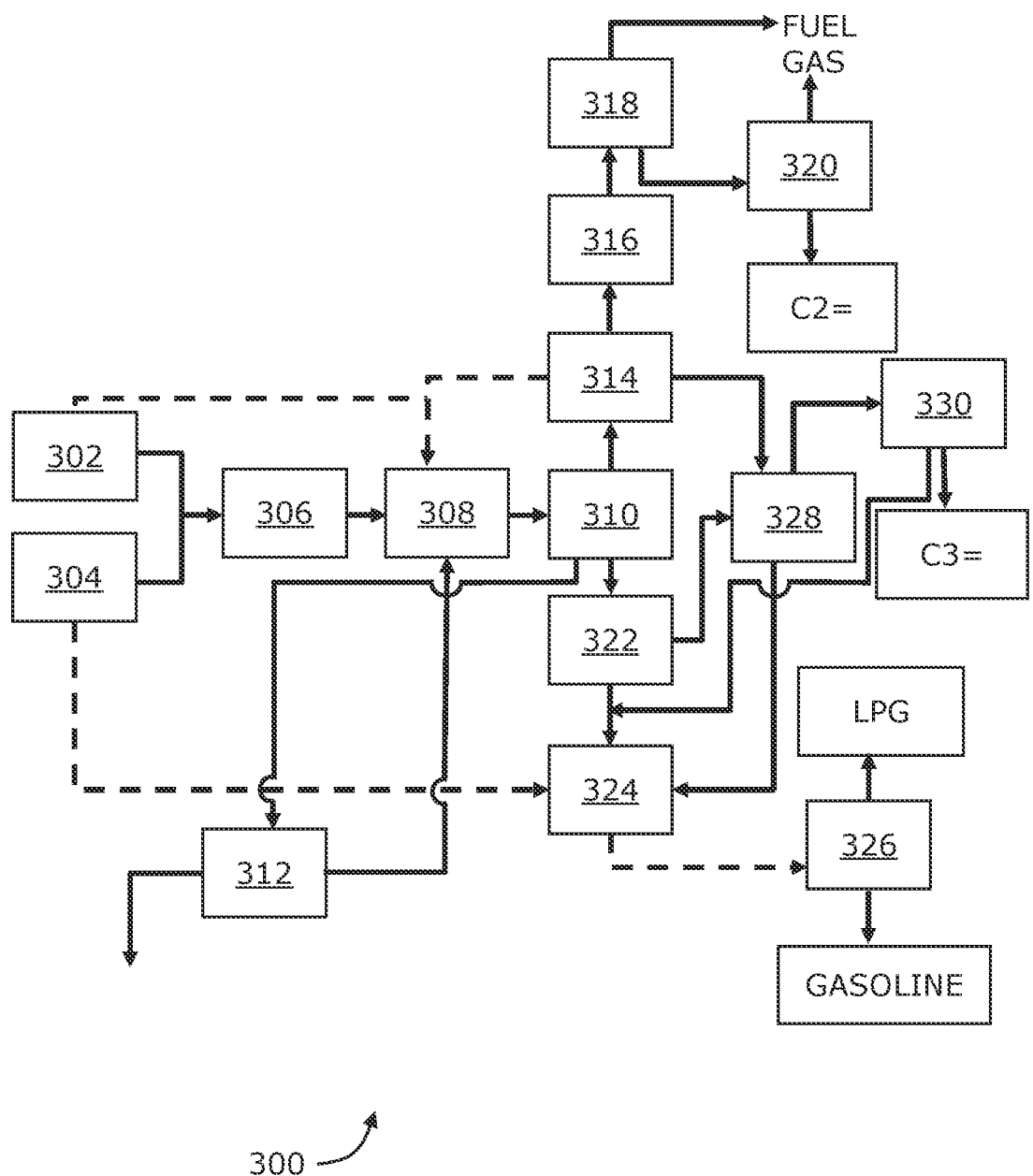
FIG. 3 is a schematic illustration of a once-through process for producing olefins and gasoline from renewable sources utilizing scrubbed $CO_2$ as a feed for Methanol-to-Olefin (MTO) reaction according to an embodiment of the present disclosure.

FIG. 3 is a schematic illustration of a once-through process 300 for producing green olefins and green gasoline from renewable sources utilizing scrubbed $CO_2$ as a feed for Methanol-to-Olefin (MTO) reaction according to an embodiment of the present disclosure. At a step 302, $CO_2$ is obtained from a $CO_2$ feed chamber. At a step 304, hydrogen is obtained from a hydrogen feed chamber. The hydrogen is produced by electrolyzing water in a water electrolyzer 312 and supplied to the hydrogen feed chamber 304 (not shown). *** At a step 306, methanol is produced in a methanol reactor by utilizing the $CO_2$ obtained from the $CO_2$ feed chamber and the Hydrogen obtained from the hydrogen feed chamber. At a step 308, the methanol is reacted in an isothermal Methanol-to-Olefin (MTO) reactor to produce an MTO reaction effluent. The non-converted $CO_2$ from the methanol reactor is directed into the isothermal Methanol-to-Olefin (MTO) reactor. At a step 310, the MTO reaction effluent is quenched by treating the MTO reaction effluent with water in a quenching chamber. At a step 312, the quenched water is supplied as a feed to the water electrolyzer. At a step 314, the $CO_2$ from the MTO reaction effluent is scrubbed using a $CO_2$ scrubber. The scrubbed $CO_2$ is directed into the isothermal Methanol-to-Olefin (MTO) reactor along with the $CO_2$ from the $CO_2$ feed chamber for the MTO reaction. At a step 316, the quenched MTO reaction effluent is reacted in a Deethanizer column for separating $C_2$ hydrocarbons from $C_{3+}$ hydrocarbons. The Deethanizer column produces a Deethanizer overhead vapor fraction that is rich in ethane and ethylene and a Deethanizer bottom fraction that is rich in $C_{3+}$ hydrocarbons. At a step 318, the Deethanizer overhead vapor fraction is treated in a Demethanizer column for separating $C_1$ hydrocarbons from $C_{2+}$ hydrocarbons. The Demethanizer column produces a Demethanizer overhead vapor fraction rich in $CH_4$, $CO_2$, $H_2$, and CO and a Demethanizer bottom fraction that is rich in $C_{2+}$ hydrocarbons comprising olefins and paraffins. The overhead vapor fraction that is rich in methane is used as fuel gas. At a step 320, $C_2$ olefins are separated from $C_2$ paraffins in a $C_2$ splitter column. The $C_2$ paraffins from the $C_2$ splitter column are used as fuel gas. At a step 322, the quenched MTO reaction effluent is reacted in a Debutanizer column for separating $C_4$ hydrocarbons from $C_{5+}$ hydrocarbons. A fraction of separated hydrocarbons comprising $C_{5+}$ hydrocarbons settles at a bottom of the Debutanizer column after the reaction. At a step 324, the fraction of separated hydrocarbons in the Debutanizer column is hydrogenated with the hydrogen from the hydrogen feed chamber. At a step 326, the hydrogenated hydrocarbons are stabilized in a gasoline stabilizer column to produce green gasoline and Liquefied Petroleum Gas (LPG). At a step 328, the Deethanizer bottom fraction that is rich in $C_{3+}$ hydrocarbons and a Debutanizer overhead vapor fraction rich in butane and butylene are treated in a Depropanizer column to produce a Depropanizer overhead vapor fraction that is rich in propane and propylene and a Depropanizer bottom fraction that is rich in $C_{4+}$ hydrocarbons. The Depropanizer bottom fraction is directed into the hydrogenation reactor for hydrogenation. At a step 330, the propylene is separated from the propane in the Depropanizer overhead vapor fraction in a $C_3$ splitter column. The propane from the $C_3$ splitter column is directed along with the fraction of separated hydrocarbons from the Debutanizer column into the hydrogenation reactor for hydrogenation.

Figure 4:
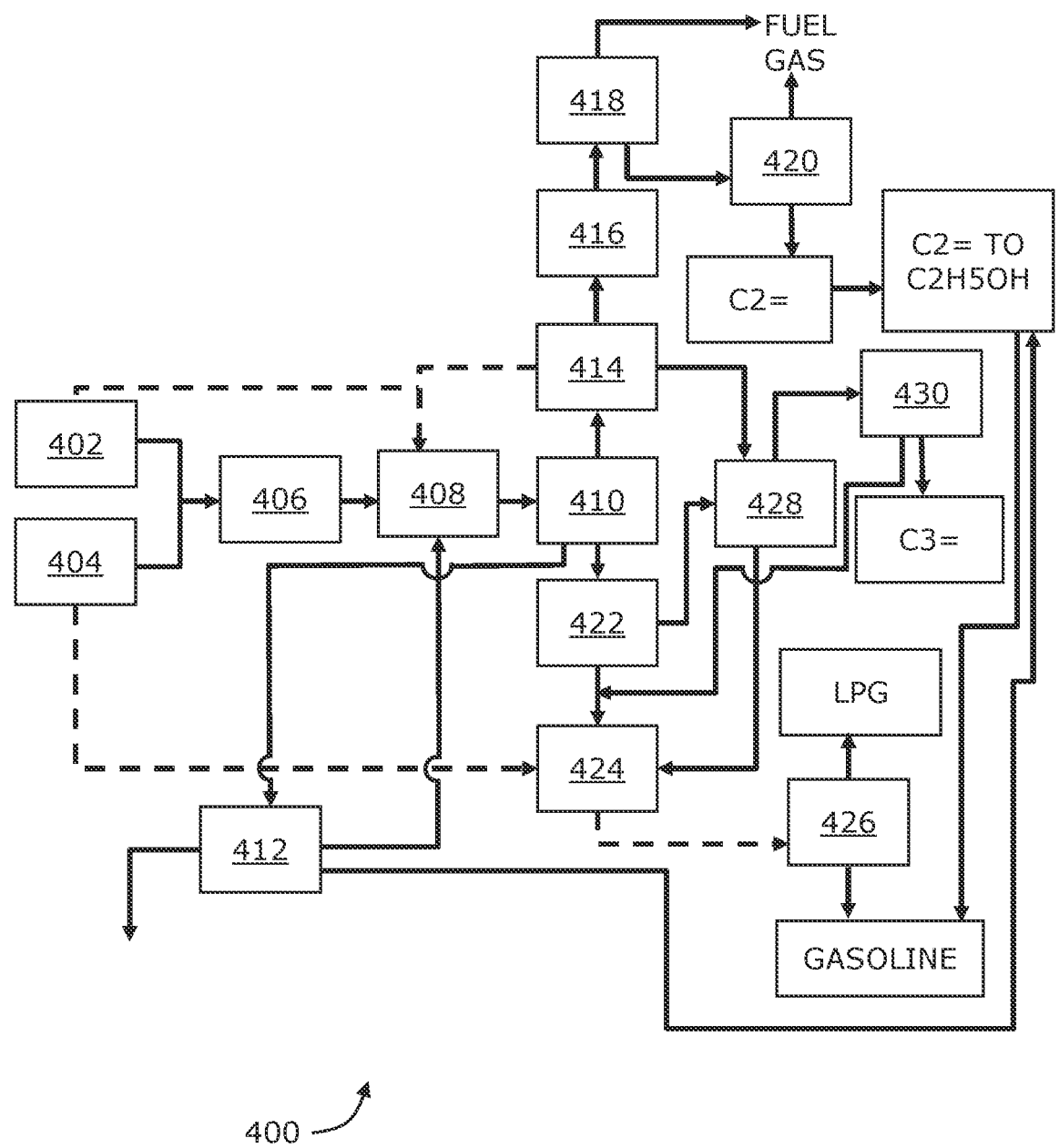
FIG. 4 is a schematic illustration of a once-through process for producing olefins and gasoline from renewable sources comprising converting green ethylene into ethyl alcohol to increase Research Octane Number (RON) and Motor Octane Number (MON) of green gasoline according to an embodiment of the present disclosure.

FIG. 4 is a schematic illustration of a once-through process 400 for producing green olefins and green gasoline from renewable sources comprising converting green ethylene into ethyl alcohol to increase Research Octane Number (RON) and Motor Octane Number (MON) of green gasoline according to an embodiment of the present disclosure. At a step 402, $CO_2$ is obtained from a $CO_2$ feed chamber. At a step 404, hydrogen is obtained from a hydrogen feed chamber. The hydrogen is produced by electrolyzing water in a water electrolyzer 412 and supplied to the hydrogen feed chamber 404 (not shown). At a step 406, methanol is produced in a methanol reactor utilizing the $CO_2$ obtained from the $CO_2$ feed chamber and the Hydrogen obtained from the hydrogen feed chamber. At a step 408, the methanol is reacted in an isothermal Methanol-to-Olefin (MTO) reactor to produce an MTO reaction effluent. The non-converted $CO_2$ from the methanol reactor is directed into the isothermal Methanol-to-Olefin (MTO) reactor. At a step 410, the MTO reaction effluent is quenched by treating the MTO reaction effluent with water in a quenching chamber. At a step 412, the quenched water is supplied as a feed to the water electrolyzer. At a step 414, $CO_2$ from the MTO reaction effluent is scrubbed using a $CO_2$ scrubber. The scrubbed $CO_2$ is directed into the isothermal MTO reactor along with the $CO_2$ from the $CO_2$ feed chamber for the MTO reaction. At a step 416, the quenched MTO reaction effluent is treated in a Deethanizer column for separating $C_2$ hydrocarbons from $C_{3+}$ hydrocarbons. The Deethanizer column produces a Deethanizer overhead vapor fraction that is rich in ethane and ethylene and a Deethanizer bottom fraction that is rich in $C_{3+}$ hydrocarbons. At a step 418, the Deethanizer overhead vapor fraction is treated in a Demethanizer column for separating $C_1$ hydrocarbons from $C_{2+}$ hydrocarbons. The Demethanizer column produces a Demethanizer overhead vapor fraction rich in $CH_4$, $CO_2$, $H_2$, and CO and a Demethanizer bottom fraction that is rich in $C_{2+}$ hydrocarbons comprising olefins and paraffins. The overhead vapor fraction that is rich in methane is used as fuel gas. At a step 420, $C_2$ olefins are separated from $C_2$ paraffins in a $C_2$ splitter column. The $C_2$ paraffins from the $C_2$ splitter column are used as fuel gas. The $C_2$ olefins are hydrated with water to produce ethanol. At a step 422, the quenched MTO reaction effluent is treated in a Debutanizer column for separating $C_4$ hydrocarbons from $C_{5+}$ hydrocarbons at the Debutanizer column. A fraction of the separated hydrocarbons comprising $C_{5+}$ hydrocarbons settles at a bottom of the Debutanizer column after separation. At a step 424, the fraction of separated hydrocarbons in the Debutanizer column is hydrogenated with the hydrogen from the hydrogen feed chamber. At a step 426, the hydrogenated hydrocarbons are stabilized in a gasoline stabilizer column to produce green gasoline and Liquefied Petroleum Gas (LPG). The ethanol is used to increase the Research Octane Number (RON) and Motor Octane Number (MON) of the green gasoline. At a step 428, the Deethanizer bottom fraction that is rich in $C_{3+}$ hydrocarbons and a Debutanizer overhead vapor fraction rich in butane and butylene are treated in a Depropanizer column to produce a Depropanizer overhead vapor fraction that is rich in propane and propylene and a Depropanizer bottom fraction that is rich in $C_{4+}$ hydrocarbons. The Depropanizer bottom fraction is directed into the hydrogenation reactor for hydrogenation. At a step 430, the propylene is separated from the propane in the Depropanizer overhead vapor fraction in a $C_3$ splitter column. The propane from the $C_3$ splitter column is directed along with the fraction of separated hydrocarbons from the Debutanizer column into the hydrogenation reactor for hydrogenation.

Figure 5:
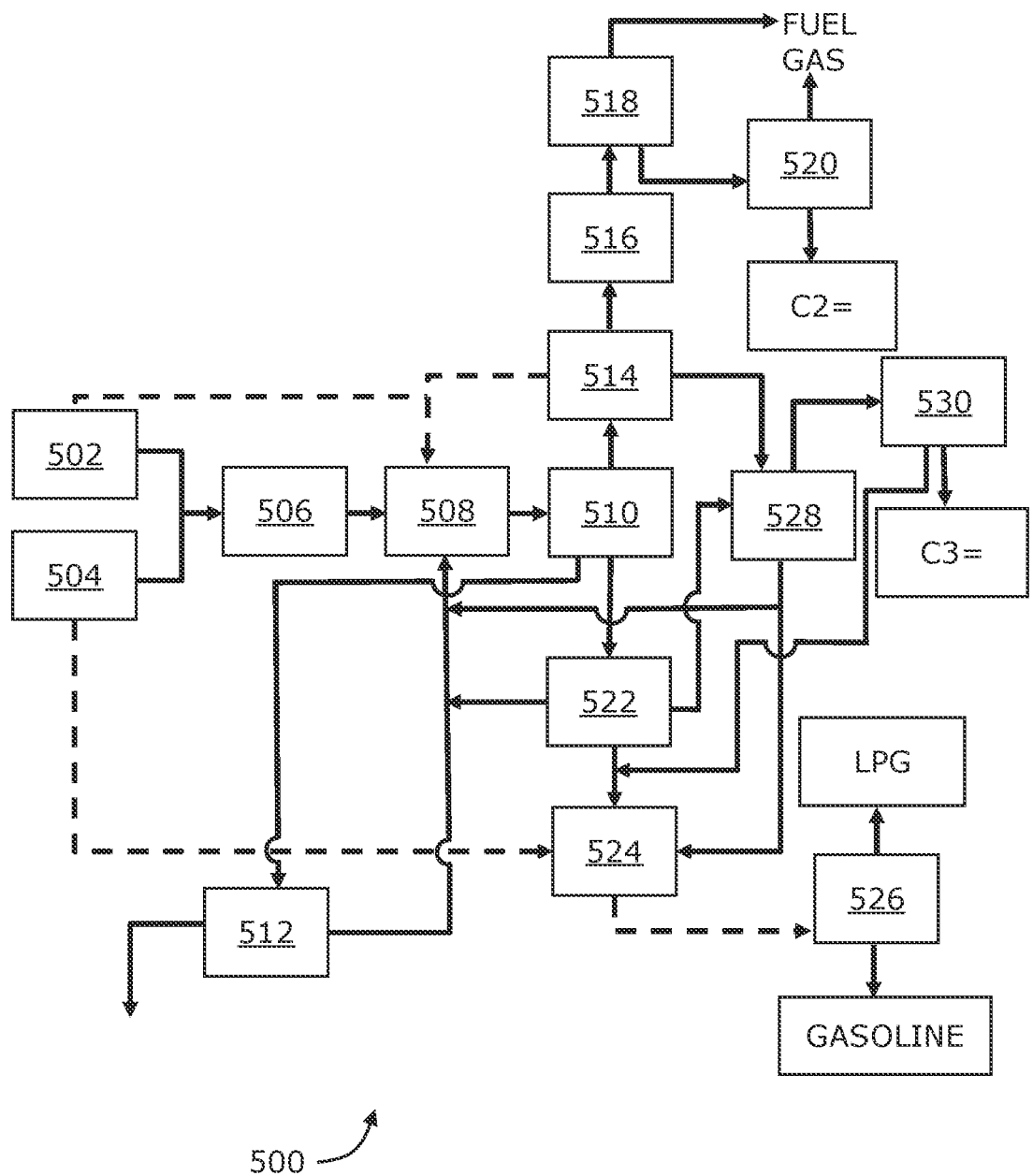
FIG. 5 is a schematic illustration of a process with recycling for producing olefins and gasoline from renewable sources comprising directing a portion of a Debutanizer and a Depropanizer bottom fraction into an isothermal Methanol-to-Olefin (MTO) reactor and utilizing scrubbed $CO_2$ as a feed for Methanol-to-Olefin (MTO) reaction according to an embodiment of the present disclosure.

FIG. 5 is a schematic illustration of a process 500 with recycling for producing green olefins and green gasoline from renewable sources comprising directing a portion of a Debutanizer and a Depropanizer bottom fraction into an isothermal Methanol-to-Olefin (MTO) reactor and utilizing scrubbed $CO_2$ as a feed for Methanol-to-Olefin (MTO) reaction according to an embodiment of the present disclosure. At a step 502, $CO_2$ is obtained from a $CO_2$ feed chamber. At a step 504, hydrogen is obtained from a hydrogen feed chamber. The hydrogen is produced by electrolyzing water in a water electrolyzer 512 and supplied to the hydrogen feed chamber 504 (not shown). At a step

506, methanol is produced in a methanol reactor utilizing the $CO_2$ obtained from the $CO_2$ feed chamber and the Hydrogen obtained from the hydrogen feed chamber. At a step 508, the methanol is reacted in an isothermal Methanol-to-Olefin (MTO) reactor to produce an MTO reaction effluent. The non-converted $CO_2$ from the methanol reactor is directed into the isothermal Methanol-to-Olefin (MTO) reactor. At a step 510, the MTO reaction effluent is quenched by treating the MTO reaction effluent with water in a quenching chamber. At a step 512, the quenched water is supplied as a feed to the water electrolyzer. At a step 514, $CO_2$ from the MTO reaction effluent is scrubbed using a $CO_2$ scrubber. The scrubbed $CO_2$ is directed into the isothermal Methanol-to-Olefin (MTO) reactor along with the $CO_2$ from the $CO_2$ feed chamber for the MTO reaction. At a step 516, the quenched MTO reaction effluent is treated in a Deethanizer column for separating $C_2$ hydrocarbons from $C_{3+}$ hydrocarbons. The Deethanizer column produces a Deethanizer overhead vapor fraction that is rich in ethane and ethylene and a Deethanizer bottom fraction that is rich in $C_{3+}$ hydrocarbons. At a step 518, the Deethanizer overhead vapor fraction is treated in a Demethanizer column for separating $C_1$ hydrocarbons from $C_{2+}$ hydrocarbons. The Demethanizer column produces a Demethanizer overhead vapor fraction rich in $CH_4$, $CO_2$, $H_2$, and CO and a Demethanizer bottom fraction that is rich in $C_{2+}$ hydrocarbons comprising olefins and paraffins. The overhead vapor fraction that is rich in methane is used as fuel gas. At a step 520, $C_2$ olefins are separated from $C_2$ paraffins in a $C_2$ splitter column. The $C_2$ paraffins from the $C_2$ splitter column are used as fuel gas. At a step 522, the quenched MTO reaction effluent is treated in a Debutanizer column for separating $C_4$ hydrocarbons from $C_{5+}$ hydrocarbons at the Debutanizer column. A fraction of separated hydrocarbons comprising $C_{5+}$ hydrocarbons settles at a bottom of the Debutanizer column after the reaction. A first fraction of the separated hydrocarbons is directed into the isothermal Methanol-to-Olefin (MTO) reactor for MTO reaction. At a step 524, remaining fraction of the separated hydrocarbons in the Debutanizer column is hydrogenated with the hydrogen from the hydrogen feed chamber. At a step 526, the hydrogenated hydrocarbons are stabilized in a gasoline stabilizer column to produce green gasoline and Liquefied Petroleum Gas (LPG). At a step 528, the Deethanizer bottom fraction that is rich in $C_{3+}$ hydrocarbons and a Debutanizer overhead vapor fraction rich in butane and butylene are treated in a Depropanizer column to produce a Depropanizer overhead vapor fraction that is rich in propane and propylene and a Depropanizer bottom fraction that is rich in $C_{4+}$ hydrocarbons. A portion of the Depropanizer bottom fraction is directed into the isothermal Methanol-to-Olefin (MTO) reactor for MTO reaction. The remaining portion of the Depropanizer bottom fraction is directed to the hydrogenation reactor for hydrogenation. At a step 530, the propylene is separated from propane in the Depropanizer overhead vapor fraction in a $C_3$ splitter column. The propane from the $C_3$ splitter is directed along with the remaining fraction of separated hydrocarbons from the Debutanizer column into the hydrogenation reactor for hydrogenation.

Figure 6:
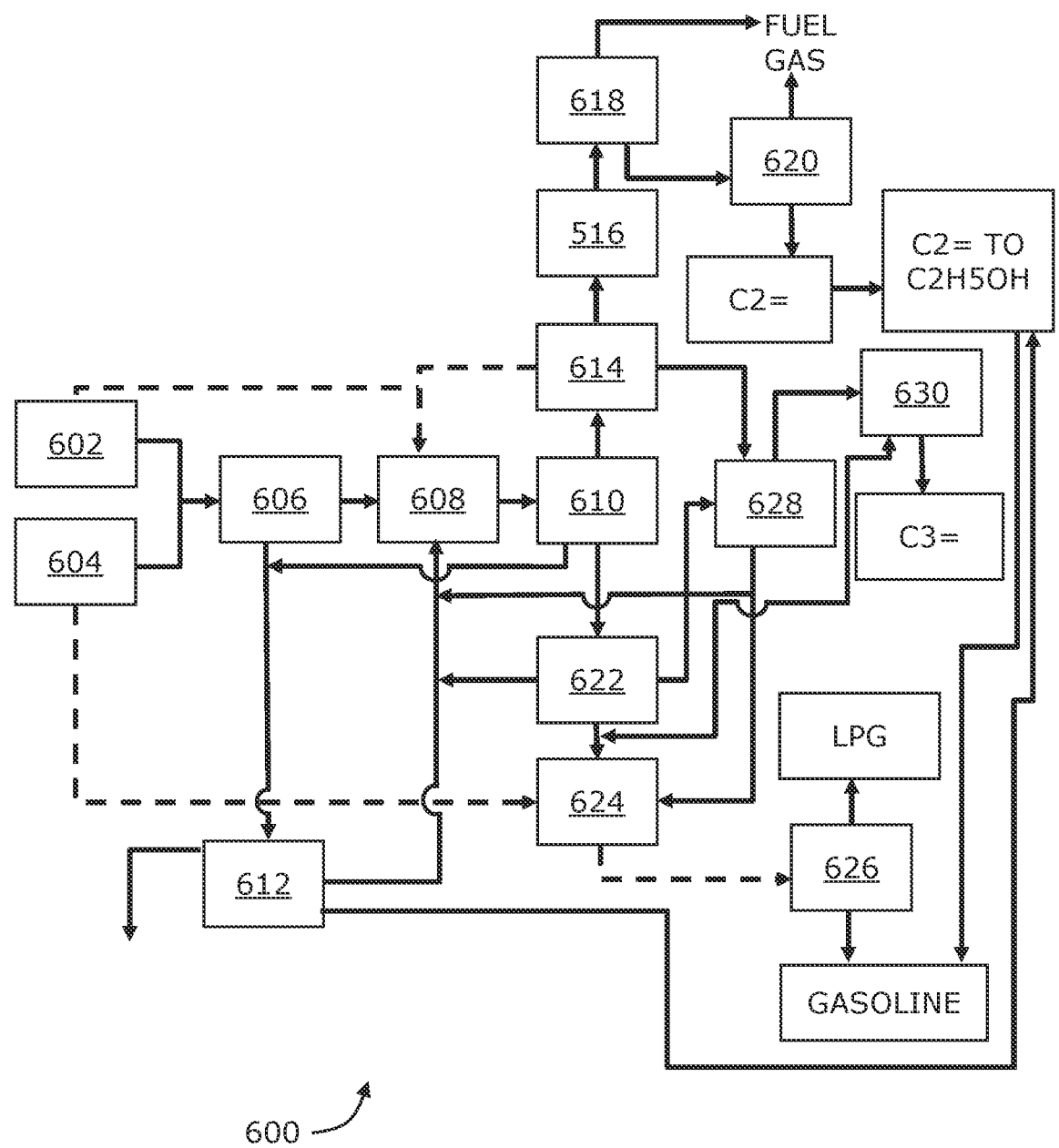
FIG. 6 is a schematic illustration of a process with recycling for producing olefins and gasoline from renewable sources comprising directing a portion of a Debutanizer and a Depropanizer bottom fraction into an isothermal Methanol-to-Olefin (MTO) reactor, utilizing scrubbed $CO_2$ as a feed for MTO and converting ethylene into ethyl alcohol to increase Research Octane Number (RON) and Motor Octane Number (MON) of gasoline according to an embodiment of the present disclosure.

FIG. 6 is a schematic illustration of a process 600 with recycling for producing green olefins and green gasoline from renewable sources comprising directing a portion of a Debutanizer and a Depropanizer bottom fraction into an isothermal Methanol-to-Olefin (MTO) reactor, utilizing scrubbed $CO_2$ as a feed for MTO and converting green ethylene into ethyl alcohol to increase Research Octane Number (RON) and Motor Octane Number (MON) of green gasoline according to an embodiment of the present disclosure. At a step 602, $CO_2$ is obtained from a $CO_2$ feed chamber. At a step 604, hydrogen is obtained from a hydrogen feed chamber. The hydrogen is produced by electrolyzing water in a water electrolyzer 612 and supplied to the hydrogen feed chamber 604 (not shown). At a step 606, methanol is produced in a methanol reactor utilizing the $CO_2$ obtained from the $CO_2$ feed chamber and the Hydrogen obtained from the hydrogen feed chamber. At a step 608, the methanol is reacted in an isothermal Methanol-to-Olefin (MTO) reactor to produce an MTO reaction effluent. The non-converted $CO_2$ from the methanol reactor is directed into the isothermal Methanol-to-Olefin (MTO) reactor. At a step 610, the MTO reaction effluent is quenched by treating the MTO reaction effluent with water in a quenching chamber. At a step 612, the quenched water is supplied as a feed to the water electrolyzer. At a step 614, $CO_2$ from the MTO reaction effluent is scrubbed using a $CO_2$ scrubber. The scrubbed $CO_2$ is directed into the isothermal Methanol-to-Olefin (MTO) reactor along with the $CO_2$ from the $CO_2$ feed chamber for the MTO reaction. At a step 616, the quenched MTO reaction effluent is treated in a Deethanizer column for separating $C_2$ hydrocarbons from $C_{3+}$ hydrocarbons. The Deethanizer column produces a Deethanizer overhead vapor fraction that is rich in ethane and ethylene and a Deethanizer bottom fraction that is rich in $C_{3+}$ hydrocarbons. At a step 618, the Deethanizer overhead vapor fraction is treated in a Demethanizer column for separating $C_1$ hydrocarbons from $C_{2+}$ hydrocarbons. The Demethanizer column produces a Demethanizer overhead vapor fraction rich in $CH_4$, $CO_2$, $H_2$, and CO and a Demethanizer bottom fraction that is rich in $C_{2+}$ hydrocarbons comprising olefins and paraffins. The overhead vapor fraction that is rich in methane is used as fuel gas. At a step 620, $C_2$ olefins are separated from $C_2$ paraffins in a $C_2$ splitter column. The $C_2$ paraffins from the $C_2$ splitter column are used as fuel gas. The $C_2$ olefins are hydrated with water to produce ethanol. At a step 622, the quenched MTO reaction effluent is treated in a Debutanizer column for separating $C_4$ hydrocarbons from $C_{5+}$ hydrocarbons at the Debutanizer column. A fraction of separated hydrocarbons comprising $C_{5+}$ hydrocarbons settles at a bottom of the Debutanizer column after the reaction. A first fraction of the separated hydrocarbons is directed into the isothermal Methanol-to-Olefin (MTO) reactor for MTO reaction. At a step 624, the remaining fraction of separated hydrocarbons in the Debutanizer column is hydrogenated with the hydrogen from the hydrogen feed chamber. At a step 626, the hydrogenated hydrocarbons are stabilized in a gasoline stabilizer column to produce green gasoline and Liquefied Petroleum Gas (LPG). The ethanol produced by hydrating $C_2$ olefins from the $C_2$ splitter is used to increase the Research Octane Number (RON) and Motor Octane Number (MON) of the green gasoline. At a step 628, the Deethanizer bottom fraction that is rich in $C_{3+}$ hydrocarbons and a Debutanizer overhead vapor fraction rich in butane and butylene are treated in a Depropanizer column to produce a Depropanizer overhead vapor fraction that is rich in propane and propylene and a Depropanizer bottom fraction that is rich in $C_{4+}$ hydrocarbons. A first portion of the Depropanizer bottom fraction is directed into the isothermal Methanol-to-Olefin (MTO) reactor for MTO reaction and the remaining portion of the Depropanizer bottom fraction is directed into the hydrogenation reactor for hydrogenation. At a step 630, the propylene is separated from propane in the Depropanizer overhead vapor fraction in a $C_3$ splitter column. The propane from the $C_3$ splitter column is directed along with the remaining fraction of separated hydrocarbons from the Debutanizer column into the hydrogenation reactor for hydrogenation.

Figure 7:
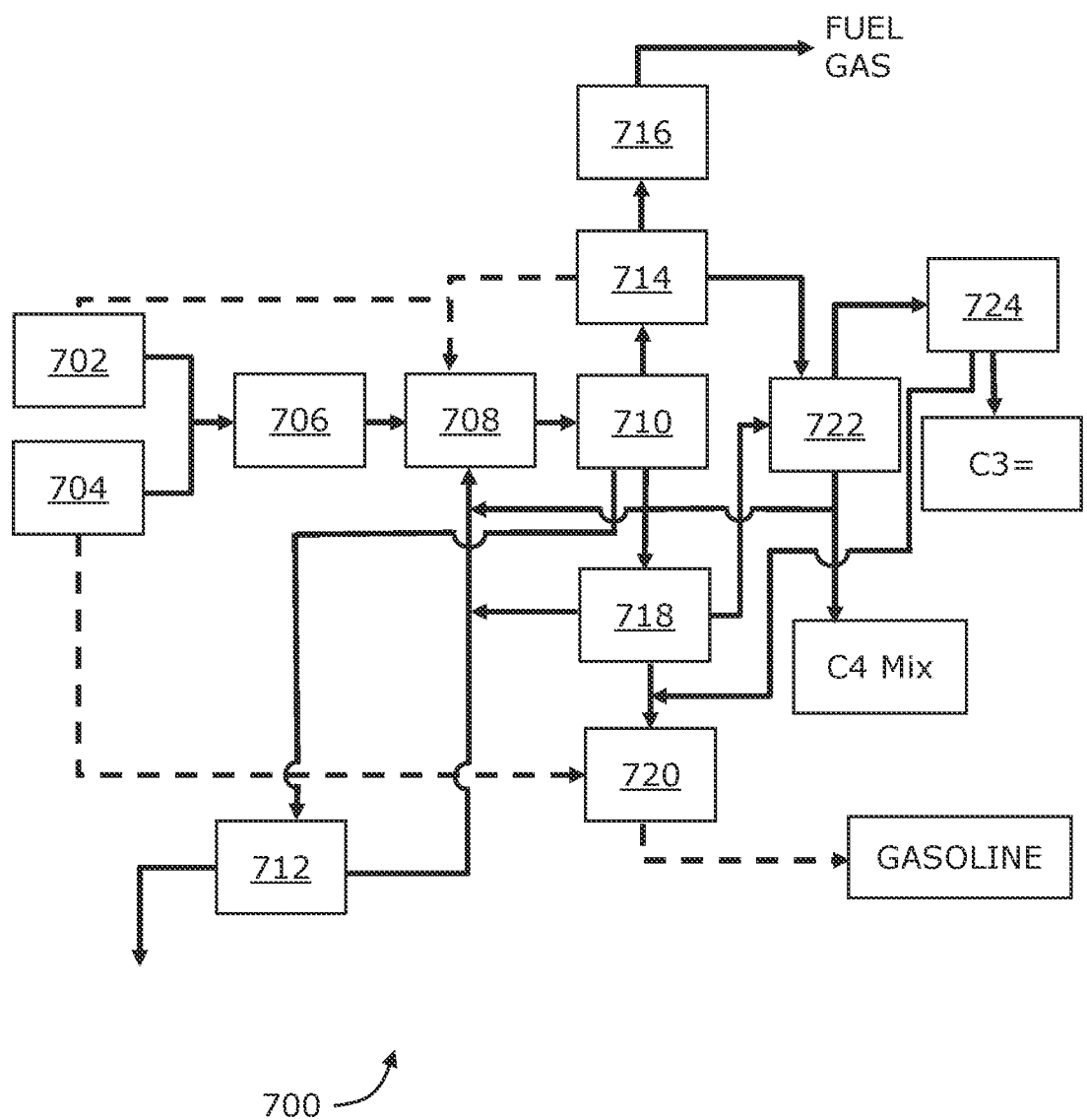
FIG. 7 is a schematic illustration of a process with recycling for producing olefins and gasoline from renewable sources comprising directing a portion of a Debutanizer and a Depropanizer bottom fraction into an isothermal Methanol-to-Olefin (MTO) reactor and obtaining a $C_4$ mix composition from a Depropanizer bottom fraction according to an embodiment of the present disclosure.

FIG. 7 is a schematic illustration of a process 700 with recycling for producing green olefins and green gasoline from renewable sources comprising directing a portion of a Debutanizer and a Depropanizer bottom fraction into an isothermal Methanol-to-Olefin (MTO) reactor and obtaining a $C_4$ mix composition from a Depropanizer bottom fraction according to an embodiment of the present disclosure. At a step 702, $CO_2$ is obtained from a $CO_2$ feed chamber. At a step 704, hydrogen is obtained from a hydrogen feed chamber. The hydrogen is produced by electrolyzing water in a water electrolyzer 712 and supplied to the hydrogen feed chamber 704 (not shown). At a step 706, methanol is produced in a methanol reactor utilizing the $CO_2$ obtained from the $CO_2$ feed chamber and the Hydrogen obtained from the hydrogen feed chamber. At a step 708, the methanol is reacted in an isothermal Methanol-to-Olefin (MTO) reactor to produce an MTO reaction effluent. The non-converted $CO_2$ from the methanol reactor is directed into the isothermal Methanol-to-Olefin (MTO) reactor. At a step 710, the MTO reaction effluent is quenched by treating the MTO reaction effluent with water in a quenching chamber. At a step 712, the quenched water is supplied as a feed to the water electrolyzer. At a step 714, $CO_2$ from the MTO reaction effluent is scrubbed using a $CO_2$ scrubber. The scrubbed $CO_2$ is directed into the isothermal MTO reactor along with the $CO_2$ from the $CO_2$ feed chamber for the MTO reaction. At a step 716, the quenched MTO reaction effluent is treated in a Deethanizer column for separating $C_2$ hydrocarbons from $C_{3+}$ hydrocarbons. The Deethanizer column produces a Deethanizer overhead vapor fraction that is rich in ethane and ethylene and a Deethanizer bottom fraction that is rich in $C_{3+}$ hydrocarbons. The Deethanizer overhead vapor fraction is used as fuel gas. At a step 718, the quenched MTO reaction effluent is treated in a Debutanizer column for separating $C_4$ hydrocarbons from $C_{5+}$ hydrocarbons. A fraction of the separated hydrocarbons comprising $C_{5+}$ hydrocarbons settles at a bottom of the Debutanizer column after separation. A portion of the separated hydrocarbons is directed into the isothermal Methanol-to-Olefin (MTO) reactor for MTO reaction. At a step 720, the remaining portion of separated hydrocarbons in the Debutanizer column is hydrogenated with the hydrogen from the hydrogen feed chamber to produce green gasoline. At a step 722, the Deethanizer bottom fraction that is rich in $C_{3+}$ hydrocarbons and a Debutanizer overhead vapor fraction rich in butane and butylene are treated in a Depropanizer column to produce a Depropanizer overhead vapor fraction that is rich in propane and propylene and a Depropanizer bottom fraction that is rich in $C_{4+}$ hydrocarbons. The Depropanizer bottom fraction may also have a considerable amount of aromatic hydrocarbons. A portion of the Depropanizer bottom fraction is directed into the isothermal Methanol-to-Olefin (MTO) reactor for MTO reaction. The remaining portion of the Depropanizer bottom fraction is obtained as a $C_4$ mix composition comprising 20-50% $C_4$ olefins and 50 to 80% $C_4$ paraffins. Higher contribution for $C_4$ olefins comes from iso-butylene with 30 to 60% of all the $C_4$ olefins in the stream and for $C_4$ paraffins, mostly iso-butane with over 60% of all the $C_4$ paraffins in the stream. At a step 724, the propylene is separated from propane in the Depropanizer overhead vapor fraction in a $C_3$ splitter column. The propane from the $C_3$ splitter column is directed along with the remaining fraction of separated hydrocarbons from the Debutanizer column into the hydrogenation reactor for hydrogenation.

Figure 8:
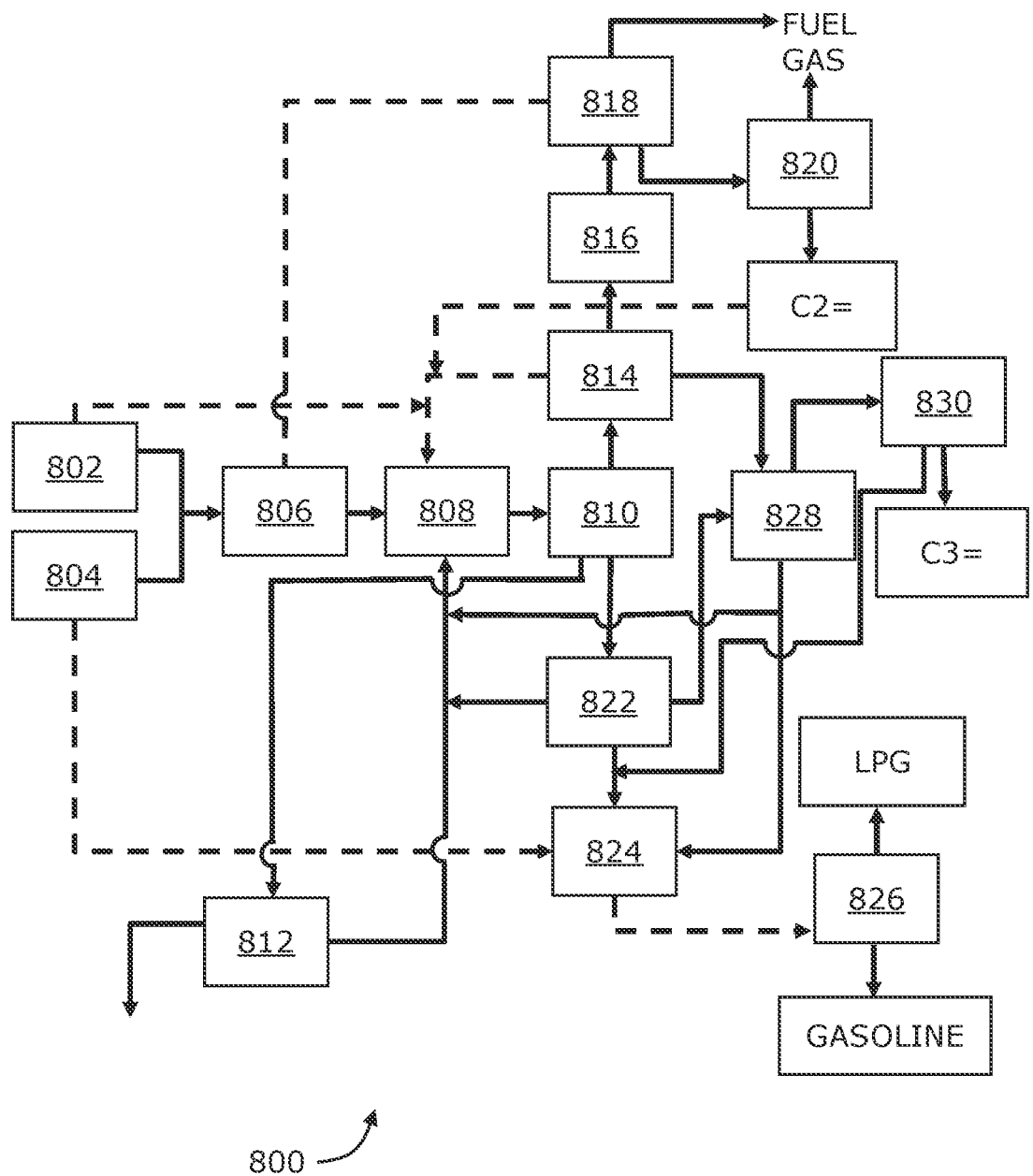
FIG. 8 is a schematic illustration of a process with complete recycling for producing olefins and gasoline from renewable sources comprising directing a portion of a Debutanizer and a Depropanizer bottom fraction and $C_2$ olefins into an isothermal Methanol-to-Olefin (MTO) reactor, utilizing scrubbed $CO_2$ as a feed for Methanol-to-Olefin (MTO) reaction, utilizing a Demethanizer overhead vapor fraction as a feed for methanol synthesis according to an embodiment of the present disclosure.

FIG. 8 is a schematic illustration of a process 800 with complete recycle for producing green olefins and green gasoline from renewable sources comprising directing a portion of a Debutanizer and a Depropanizer bottom fraction and $C_2$ olefins into an isothermal Methanol-to-Olefin (MTO) reactor, utilizing scrubbed $CO_2$ as a feed for MTO (Methanol-to-Olefin) reaction, utilizing a Demethanizer overhead vapor fraction as a feed for methanol synthesis according to an embodiment of the present disclosure. At a step 802, $CO_2$ is obtained from a $CO_2$ feed chamber. At a step 804, hydrogen is obtained from a hydrogen feed chamber. The hydrogen is produced by electrolyzing water in a water electrolyzer 812 and supplied to the hydrogen feed chamber 804 (not shown). At a step 806, methanol is produced in a methanol reactor utilizing the $CO_2$ obtained from the $CO_2$ feed chamber and the Hydrogen obtained from the hydrogen feed chamber. At a step 808, the methanol is reacted in an isothermal Methanol-to-Olefin (MTO) reactor to produce an MTO reaction effluent. The non-converted $CO_2$ from the methanol reactor is directed into the isothermal MTO reactor. At a step 810, the MTO reaction effluent is quenched by treating the MTO reaction effluent with water in a quenching chamber. At a step 812, the quenched water is supplied as a feed to the water electrolyzer. At a step 814, $CO_2$ from the MTO reaction effluent is scrubbed using a $CO_2$ scrubber. The scrubbed $CO_2$ is directed into the isothermal MTO reactor along with the $CO_2$ from the $CO_2$ feed chamber for the MTO reaction. At a step 816, the quenched MTO reaction effluent is treated in a Deethanizer column for separating $C_2$ hydrocarbons from $C_{3+}$ hydrocarbons. The Deethanizer column produces a Deethanizer overhead vapor fraction that is rich in ethane and ethylene and a Deethanizer bottom fraction that is rich in $C_{3+}$ hydrocarbons. At a step 818, the Deethanizer overhead vapor fraction is treated in a Demethanizer column for separating $C_1$ hydrocarbons from $C_{2+}$ hydrocarbons. The Demethanizer column produces a Demethanizer overhead vapor fraction rich in $CH_4$, $CO_2$, $H_2$, and CO and a Demethanizer bottom fraction that is rich in $C_{2+}$ hydrocarbons comprising olefins and paraffins. A portion of the Demethanizer overhead vapor fraction is directed as a feed for producing methanol into the methanol reactor. The portion of the Demethanizer overhead vapor fraction that is rich in methane is used as fuel gas. At a step 820, $C_2$ olefins are separated from $C_2$ paraffins in a $C_2$ splitter column. The $C_2$ paraffins from the $C_2$ splitter column are used as fuel gas. The separated $C_2$ olefins from the $C_2$ splitter is directed into the isothermal Methanol-to-Olefin (MTO) reactor for MTO reaction. At a step 822, the quenched MTO reaction effluent is teated in a Debutanizer column for separating $C_4$ hydrocarbons from $C_{5+}$ hydrocarbons at the Debutanizer column. A fraction of the separated hydrocarbons settles at a bottom of the Debutanizer column after separation. A portion of the separated hydrocarbons is directed into the isothermal Methanol-to-Olefin (MTO) reactor for MTO reaction. At a step 824, the remaining portion of separated hydrocarbons in the Debutanizer column is hydrogenated with the hydrogen from the hydrogen feed chamber. The fraction of separated hydrocarbons from the Debutanizer column comprises $C_{5+}$ hydrocarbons. At a step 826, the hydrogenated hydrocarbons are stabilized in a gasoline stabilizer column to produce green gasoline and Liquefied Petroleum Gas (LPG). At a step 828, the Deethanizer bottom fraction that is rich in $C_{3+}$ hydrocarbons and a Debutanizer overhead vapor fraction rich in butane and butylene are treated in a Depropanizer column to produce a Depropanizer overhead vapor fraction that is rich in propane and propylene and a Depropanizer bottom fraction that is rich in $C_{4+}$ hydrocarbons. The Depropanizer bottom fraction may also have a considerable amount of $C_5$ to $C_9$ hydrocarbons (olefins+paraffins) and aromatic hydrocarbons. A portion of the Depropanizer bottom fraction is directed into the isothermal Methanol-to-Olefin (MTO) reactor for MTO reaction. Remaining portion of the Depropanizer bottom fraction is directed to the hydrogenation reactor for hydrogenation. At a step 830, the propylene is separated from propane in the Depropanizer overhead vapor fraction in a $C_3$ splitter column. The propane from the $C_3$ splitter column is directed along with the remaining fraction of separated hydrocarbons from the Debutanizer column into the hydrogenation reactor for hydrogenation.

Figure 9:
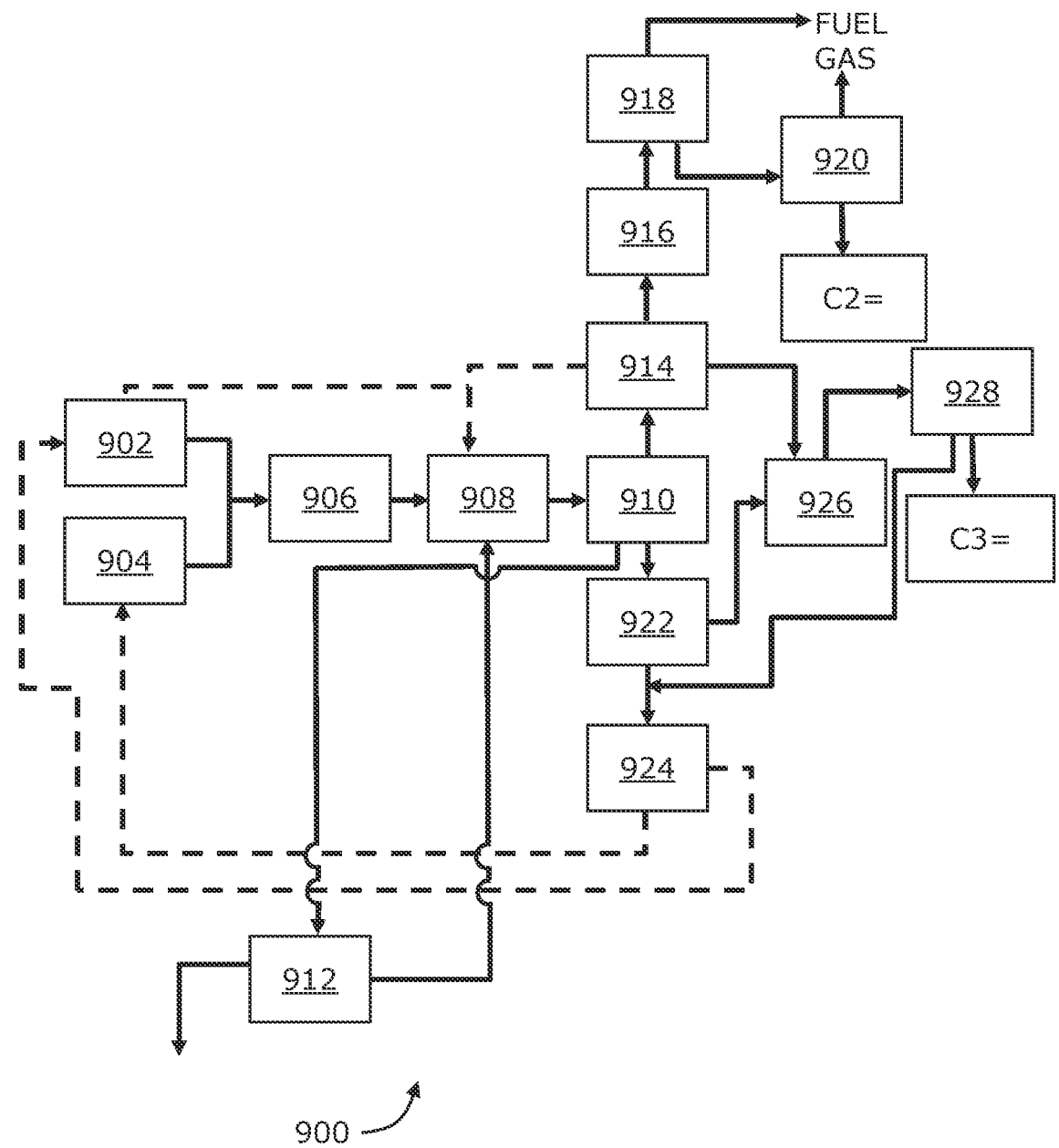
FIG. 9 is a schematic illustration of a once-through process for producing olefins and gasoline from renewable sources comprising gasification of a Debutanizer bottom fraction and utilizing products of the gasification comprising hydrogen and $CO_2$ as additional feed for producing methanol according to an embodiment of the present disclosure.

FIG. 9 is a schematic illustration of a once-through process 900 for producing green olefins and green gasoline from renewable sources comprising gasification of a Debutanizer bottom fraction and utilizing products of the gasification comprising hydrogen and $CO_2$ as additional feed for producing methanol according to an embodiment of the present disclosure. At a step 902, $CO_2$ is obtained from a $CO_2$ feed chamber. At a step 904, hydrogen is obtained from a hydrogen feed chamber. The hydrogen is produced by electrolyzing water in a water electrolyzer 912 and supplied to the hydrogen feed chamber 904 (not shown). At a step 906, methanol is produced in a methanol reactor utilizing the $CO_2$ obtained from the $CO_2$ feed chamber and the Hydrogen obtained from the hydrogen feed chamber. At a step 908, the methanol is reacted in an isothermal Methanol-to-Olefin (MTO) reactor to produce an MTO reaction effluent. The non-converted $CO_2$ from the methanol reactor is directed into the isothermal Methanol-to-Olefin (MTO) reactor. At a step 910, the MTO reaction effluent is quenched by treating the MTO reaction effluent with water in a quenching chamber. At a step 912, the quenched water is supplied as a feed to the water electrolyzer. At a step 914, $CO_2$ from the MTO reaction effluent is scrubbed using a $CO_2$ scrubber. The scrubbed $CO_2$ is directed into the isothermal Methanol-to-Olefin (MTO) reactor along with the $CO_2$ from the $CO_2$ feed chamber for the MTO reaction. At a step 916, the quenched MTO reaction effluent is treated in a Deethanizer column for separating $C_2$ hydrocarbons from $C_{3+}$ hydrocarbons. The Deethanizer column produces a Deethanizer overhead vapor fraction that is rich in ethane and ethylene and a Deethanizer bottom fraction that is rich in $C_{3+}$ hydrocarbons. At a step 918, the Deethanizer overhead vapor fraction is treated in a Demethanizer column for separating $C_1$ hydrocarbons from $C_{2+}$ hydrocarbons. The Demethanizer column produces a Demethanizer overhead vapor fraction rich in $CH_4$, $CO_2$, $H_2$, and CO and a Demethanizer bottom fraction that is rich in $C_{2+}$ hydrocarbons comprising olefins and paraffins. A portion of the Demethanizer overhead vapor fraction is directed into the methanol reactor for methanol synthesis. The remaining portion of Demethanizer overhead vapor fraction that is rich in methane is used as fuel gas. At a step 920, $C_2$ olefins are separated from $C_2$ paraffins in a $C_2$ splitter column. The $C_2$ olefins are directed into the isothermal Methanol-to-Olefin (MTO) reactor and used as a feed for MTO (Methanol-to-Olefin) reaction. The $C_2$ paraffins from the $C_2$ splitter column are used as fuel gas. At a step 922, the quenched MTO reaction effluent is treated in a Debutanizer column for separating $C_4$ hydrocarbons from $C_{5+}$ hydrocarbons at the Debutanizer column. A fraction of the separated hydrocarbons comprising $C_{5+}$ hydrocarbons settles at a bottom of the Debutanizer column after separation. At a step 924, the separated hydrocarbons comprising the $C_{5+}$ hydrocarbons in the Debutanizer column are subjected to gasification in a gasification reactor. The products of the gasification comprise hydrogen and $CO_2$. The hydrogen is directed into the hydrogen feed chamber and the $CO_2$ is directed into the $CO_2$ feed chamber. The products of the gasification comprising hydrogen and $CO_2$ are used as additional feed for producing the methanol in the methanol reactor. At a step 926, the Deethanizer bottom fraction that is rich in $C_{3+}$ hydrocarbons and a Debutanizer overhead vapor fraction rich in butane and butylene are treated in a Depropanizer column to produce a Depropanizer overhead vapor fraction that is rich in propane and propylene and a Depropanizer bottom fraction that is rich in $C_{4+}$ hydrocarbons. The Depropanizer bottom fraction may also have a considerable amount of $C_5$ to $C_9$ hydrocarbons (olefins+paraffins) and aromatic hydrocarbons. A portion of the Depropanizer bottom fraction is directed into the isothermal Methanol-to-Olefin (MTO) reactor for MTO reaction. Remaining portion of the Depropanizer bottom fraction is directed to the hydrogenation reactor for hydrogenation. At a step 928, the propylene is separated from propane in the Depropanizer overhead vapor fraction in a $C_3$ splitter column. The propane from the $C_3$ splitter column is directed along with the fraction of separated hydrocarbons from the Debutanizer column in the gasification reactor for gasification.

Figure 10:
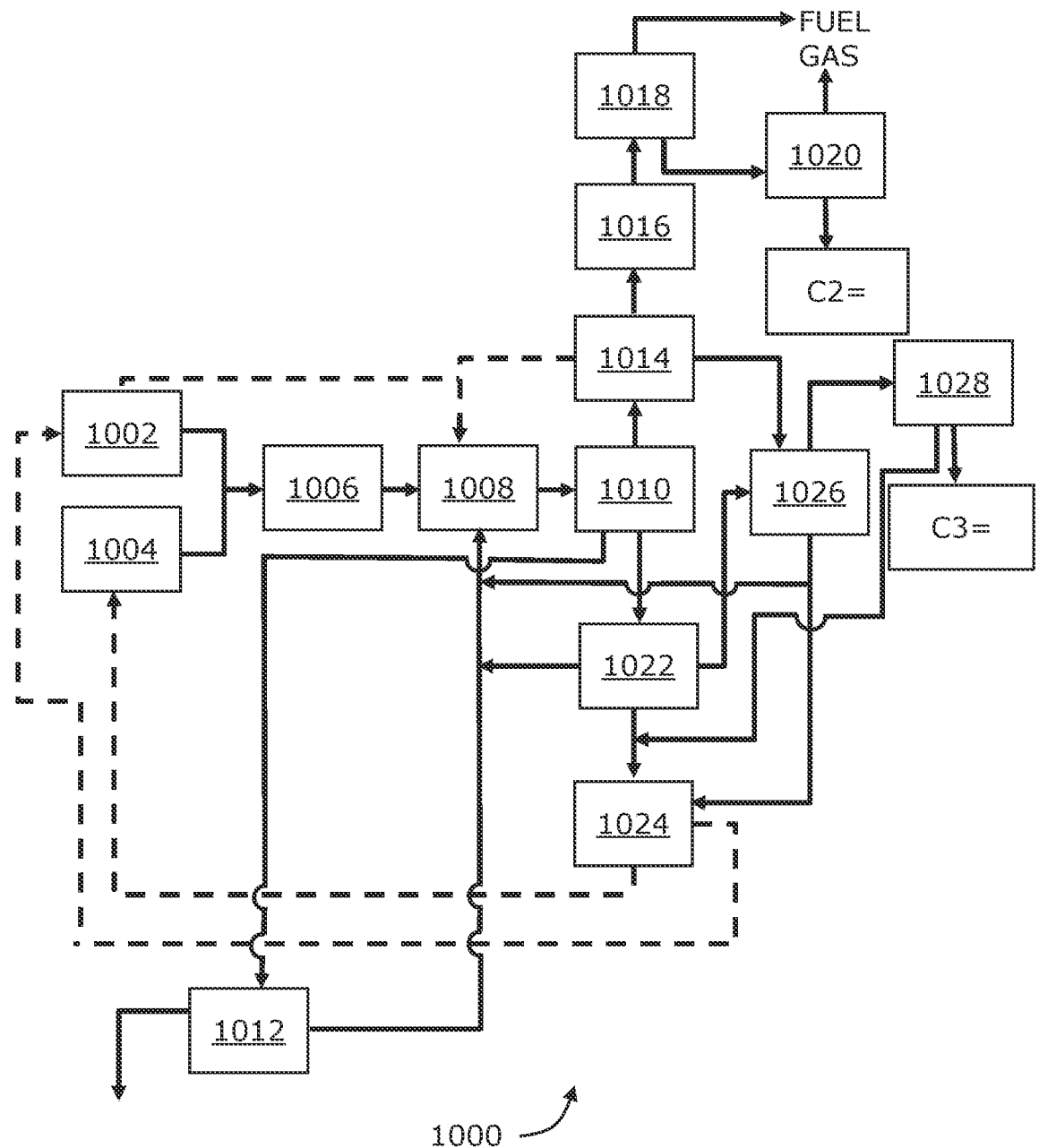
FIG. 10 is a schematic illustration of a process with recycling for producing olefins and gasoline from renewable sources comprising directing a portion of a Debutanizer and a Depropanizer bottom fraction into an isothermal Methanol-to-Olefin (MTO) reactor, gasification of a Debutanizer bottom fraction, and utilizing products of the gasification comprising hydrogen and $CO_2$ as additional feed for producing methanol according to an embodiment of the present disclosure.

FIG. 10 is a schematic illustration of a process 1000 with recycling for producing green olefins and green gasoline from renewable sources comprising directing a portion of a Debutanizer and a Depropanizer bottom fraction into an isothermal Methanol-to-Olefin (MTO) reactor, gasification of a Debutanizer bottom fraction, and utilizing products of the gasification comprising hydrogen and $CO_2$ as additional feed for producing methanol according to an embodiment of the present disclosure. At a step 1002, $CO_2$ is obtained from a $CO_2$ feed chamber. At a step 1004, hydrogen is obtained from a hydrogen feed chamber. The hydrogen is produced by electrolyzing water in a water electrolyzer 1012 and supplied to the hydrogen feed chamber 1004 (not shown). At a step 1006, methanol is produced in a methanol reactor utilizing the $CO_2$ obtained from the $CO_2$ feed chamber and the Hydrogen obtained from the hydrogen feed chamber. At a step 1008, the methanol is reacted in an isothermal Methanol-to-Olefin (MTO) reactor to produce an MTO reaction effluent. The non-converted $CO_2$ from the methanol reactor is directed into the isothermal Methanol-to-Olefin (MTO) reactor. At a step 1010, the MTO reaction effluent is quenched by treating the MTO reaction effluent with water in a quenching chamber. At a step 1012, the quenched water is supplied as a feed to the water electrolyzer. At a step 1014, $CO_2$ from the MTO reaction effluent is scrubbed using a $CO_2$ scrubber. The scrubbed $CO_2$ is directed into the isothermal Methanol-to-Olefin (MTO) reactor along with the $CO_2$ from the $CO_2$ feed chamber for the MTO reaction. At a step 1016, the quenched MTO reaction effluent is treated in a Deethanizer column for separating $C_2$ hydrocarbons from $C_{3+}$ hydrocarbons. The Deethanizer column produces a Deethanizer overhead vapor fraction that is rich in ethane and ethylene and a Deethanizer bottom fraction that is rich in $C_{3+}$ hydrocarbons. At a step 1018, the Deethanizer overhead vapor fraction is treated in a Demethanizer column for separating $C_1$ hydrocarbons from $C_{2+}$ hydrocarbons. The Demethanizer column produces a Demethanizer overhead vapor fraction rich in $CH_4$, $CO_2$, $H_2$, and CO and a Demethanizer bottom fraction that is rich in $C_{2+}$ hydrocarbons comprising olefins and paraffins. A portion of the Demethanizer overhead vapor fraction is directed into the methanol reactor for methanol synthesis. Remaining portion of the Demethanizer overhead vapor fraction that is rich in methane is used as fuel gas. At a step 1020, $C_2$ olefins are separated from $C_2$ paraffins in a $C_2$ splitter column. The $C_2$ olefins are directed into the isothermal Methanol-to-Olefin (MTO) reactor and used as a feed for MTO (Methanol-to-Olefin) reaction. The $C_2$ paraffins from the $C_2$ splitter column are used as fuel gas. At a step 1022, the quenched MTO reaction effluent is treated in a Debutanizer column for separating $C_4$ hydrocarbons from $C_{5+}$ hydrocarbons at the Debutanizer column. A fraction of the separated hydrocarbons settles at a bottom of the Debutanizer column after separation. At a step 1024, the separated hydrocarbons comprising $C_{5+}$ hydrocarbons in the Debutanizer column are subjected to gasification in a gasification reactor. The products of the gasification comprise hydrogen and $CO_2$. The hydrogen is directed into the hydrogen feed chamber and the $CO_2$ is directed into the $CO_2$ feed chamber. The products of the gasification comprising hydrogen and $CO_2$ are used as additional feed for producing the methanol in the methanol reactor. At a step 1026, the Deethanizer bottom fraction that is rich in $C_{3+}$ hydrocarbons and a Debutanizer overhead vapor fraction rich in butane and butylene are treated in a Depropanizer column to produce a Depropanizer overhead vapor fraction that is rich in propane and propylene and a Depropanizer bottom fraction that is rich in $C_{4+}$ hydrocarbons. The Depropanizer bottom fraction may also have a considerable amount of $C_5$ to $C_9$ hydrocarbons (olefins+ paraffins) and aromatic hydrocarbons. A portion of the Depropanizer bottom fraction is directed into the isothermal Methanol-to-Olefin (MTO) reactor for MTO reaction. Remaining portion of the Depropanizer bottom fraction is directed to the gasification reactor for gasification. At a step 1028, the propylene is separated from propane in the Depropanizer overhead vapor fraction in a $C_3$ splitter column. The propane from the $C_3$ splitter column is directed along with the fraction of separated hydrocarbons from the Debutanizer column in the gasification reactor for gasification.

Modifications to embodiments of the present disclosure described in the foregoing are possible without departing from the scope of the present disclosure as defined by the accompanying claims. Expressions such as "including", "comprising", "incorporating", "have", "is" used to describe, and claim the present disclosure are intended to be construed in a non-exclusive manner, namely allowing for items, components or elements not explicitly described also to be present. Reference to the singular is also to be construed to relate to the plural.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for producing olefins and gasoline from renewable sources, the method comprising:
    reacting water in a water electrolyzer to produce a first portion and a second portion of hydrogen;
    reacting carbon dioxide and the first portion of hydrogen in a methanol reactor to produce an effluent comprising methanol, water, and non-converted carbon dioxide;
    separating the effluent to produce a non-converted carbon dioxide stream and a remaining effluent stream comprising methanol and water;
    passing the remaining effluent stream and a first portion of the non-converted carbon dioxide stream to a methanol-to olefin (MTO) reactor to produce a MTO reaction effluent comprising olefinic and non-olefinic hydrocarbons, carbon dioxide, and water,
        wherein an amount of water in the remaining effluent stream is proportionally reduced relative to the amount of non-converted carbon dioxide passed to the MTO reactor, and
        wherein a first portion of the water from the MTO reaction effluent is recycled as feed to the water electrolyzer;
    separating the MTO reaction effluent by performing the following steps:
        passing the MTO effluent to a Deethanizer column to separate a $C_{2-}$ hydrocarbon stream from a $C_{3+}$ hydrocarbon,
        passing the $C_{2-}$ hydrocarbon stream to a $C_2$ splitter to separate ethylene,
        passing the $C_{3+}$ hydrocarbon stream to a Depropanizer to separate a $C_3$ hydrocarbon stream from a $C_{4+}$ hydrocarbon stream,
        passing the $C_3$ hydrocarbon stream to a $C_3$ splitter to separate propylene as an olefin product, and
        passing the $C_{4+}$ hydrocarbon stream to a Debutanizer to separate a $C_4$ overhead fraction and a $C_{5+}$ Debutanizer bottom fraction;
    hydrogenating at least a portion of the $C_{5+}$ Debutanizer bottom fraction in a hydrogenation reactor with the second portion of hydrogen to obtain a hydrogenated Debutanizer bottom fraction,
        wherein a second portion of the non-converted carbon dioxide stream is used as a diluting agent for the hydrogenation; and either
    (i) routing out at least a portion of the hydrogenated Debutanizer bottom fraction as gasoline product; or
    (ii) separating the hydrogenated Debutanizer bottom fraction in a gasoline stabilizer column to produce an LPG product as an overhead stream and a stabilized gasoline product as a bottom stream.

2. The method of claim 1, wherein the $C_4$ overhead fraction comprises 20-50% of C4 olefins and 50 to 80% of C4 paraffins.

3. The method according to claim 1, wherein the $C_3$ splitter also produces a propane stream, and
    passing at least a portion of the propane stream to the hydrogenation reactor.

4. The method according to claim 3, wherein at least a part of the ethylene is converted into ethanol and added to the gasoline product or stabilized gasoline product to increase the Research Octane Number (RON) and/or the Motor Octane Number (MON) of the gasoline.

5. The method according to claim 2, wherein the method further comprises scrubbing the carbon dioxide from the MTO reaction effluent using a carbon dioxide scrubber, wherein at least a part of the scrubbed carbon dioxide is provided as feed into the methanol reactor.

6. The method according to claim 1, further comprising passing the $C_{2-}$ stream to a Demethanizer column to produce an overhead fraction comprising methane and a bottoms fraction comprising $C_2$, and passing the bottoms fraction as the stream to the $C_2$ splitter.

7. The method according to claim 6, further comprising directing at least a part of the overhead fraction comprising methane into the methanol reactor.

8. The method according to claim 1, wherein the method further comprises quenching the MTO reaction effluent by treating the MTO reaction effluent with water before separating the MTO reaction effluent, wherein the water after quenching is directed at least partially into the water electrolyzer.

9. The method according to claim 1, wherein the carbon dioxide fed to the methanol reactor is free of sulfur components and amines.

10. The method according to claim 1, wherein the remaining effluent stream comprising methanol is purified in a distillation column which is operated under a pressure ranging between 25 bar to 125 bar, and a temperature ranging between 200° C. and 350° C.

11. The method according to claim 1, wherein the effluent from the methanol reactor prior to separation comprises a methanol-water mixture comprising 62 to 66 weight by percentage (wt-%) of methanol and about 34 to 38 weight by percentage (wt-%) of water.

12. The method according to claim 1, wherein the non-converted carbon dioxide stream further comprises hydrogen.

13. The method according to claim 1, wherein the non-converted carbon dioxide that is directed into the MTO reactor optimizes a partial pressure of reactants in the MTO reactor and increases a lifetime of a catalyst included in the isothermal MTO reactor.

14. The method according to claim 1, wherein the method includes performing the MTO reaction in the MTO reactor at a temperature in a range of 400 to 550° C. and at a pressure in a range of 0,2 to 5 bara to increase the $C_3$ hydrocarbons yield in the MTO reaction effluent.

* * * * *